US011904096B2

(12) United States Patent
Allum et al.

(10) Patent No.: US 11,904,096 B2
(45) Date of Patent: Feb. 20, 2024

(54) NASAL INTERFACE APPARATUS AND SYSTEMS FOR USE WITH A RESPIRATORY ASSIST DEVICE

(71) Applicant: Inogen, Inc., Goleta, CA (US)

(72) Inventors: Todd W. Allum, Livermore, CA (US); Gregory J. Kapust, San Ramon, CA (US)

(73) Assignee: Inogen, Inc., Goleta, CA (US)

( * ) Notice: Subject to any disclaimer, the term of this patent is extended or adjusted under 35 U.S.C. 154(b) by 876 days.

(21) Appl. No.: 16/752,556

(22) Filed: Jan. 24, 2020

(65) Prior Publication Data

US 2020/0155783 A1    May 21, 2020

Related U.S. Application Data

(63) Continuation-in-part of application No. 16/275,255, filed on Feb. 13, 2019, now Pat. No. 11,376,387, (Continued)

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0003* (2014.02); *A61M 16/0063* (2014.02);
(Continued)

(58) Field of Classification Search
CPC ............ A61M 16/101; A61M 16/0063; A61M 16/022
See application file for complete search history.

(56) References Cited

U.S. PATENT DOCUMENTS 8,136,525 B2    3/2012  Lubke et al.
D662,200 S      6/2012  Eghbal et al.
(Continued)

FOREIGN PATENT DOCUMENTS

CN    2798975 Y       7/2006
CN    101653632 A     2/2010
(Continued)

OTHER PUBLICATIONS

Search Report and Written Opinion received in International Application No. PCT/US2013/056702, dated Jan. 16, 2014.
(Continued)

*Primary Examiner* — Margaret M Luarca
(74) *Attorney, Agent, or Firm* — Knobbe Martens Olson & Bear LLP

(57) ABSTRACT

An ambulatory assist ventilation (AAV) apparatus and system are disclosed for the delivery of a respiratory gas to assist the spontaneous breathing effort of a patient with a breathing disorder. The AAV system includes a compressed respiratory gas source, a respiratory assist device for controlling respiratory gas flow to the patient, a patient circuit tubing and a low profile nasal interface device, which does not have a dead space or hollow area where CO2 can collect, for delivering the respiratory gas to the patient, wherein the nasal interface device is fluidly connected to the respiratory assist device via tubing for receiving the respiratory gas therefrom. In some cases, the nasal interface device may be used in combination with other gas sources, such as oxygen concentrators, to provide dual therapy capability suitable for some applications.

10 Claims, 24 Drawing Sheets

Related U.S. Application Data which is a continuation of application No. 14/427,986, filed as application No. PCT/US2013/056702 on Aug. 27, 2013, now Pat. No. 10,384,028.

(60) Provisional application No. 62/796,563, filed on Jan. 24, 2019, provisional application No. 61/699,969, filed on Sep. 12, 2012.

(51) Int. Cl.
*A61M 16/20* (2006.01)
*A61M 16/08* (2006.01)

(52) U.S. Cl.
CPC ...... *A61M 16/022* (2017.08); *A61M 16/0605* (2014.02); *A61M 16/0622* (2014.02); *A61M 16/0677* (2014.02); *A61M 16/201* (2014.02); *A61M 16/204* (2014.02); *A61M 16/0833* (2014.02); *A61M 16/0866* (2014.02); *A61M 2016/0021* (2013.01); *A61M 2016/0027* (2013.01); *A61M 2202/0208* (2013.01); *A61M 2205/3331* (2013.01); *A61M 2210/0618* (2013.01)

(56) References Cited

U.S. PATENT DOCUMENTS

| | | |
|---|---|---|
| 8,753,435 B2 | 6/2014 | Atlas et al. |
| 9,132,250 B2 | 9/2015 | Allum et al. |
| 9,180,270 B2 | 11/2015 | Kapust et al. |
| 9,227,034 B2 | 1/2016 | Kapust et al. |
| 9,675,774 B2 | 6/2017 | Cipollone et al. |
| 9,730,830 B2 | 8/2017 | Foley et al. |
| 9,962,512 B2 | 5/2018 | Cipollone et al. |
| 10,046,133 B2 | 8/2018 | Kapust et al. |
| 10,232,136 B2 | 3/2019 | Kapust et al. |
| 10,384,028 B2 | 8/2019 | Allum et al. |
| 11,376,387 B2 | 7/2022 | Allum et al. |
| 2002/0029004 A1 | 3/2002 | Starr et al. |
| 2005/0126574 A1 | 6/2005 | Wood |
| 2005/0241644 A1 | 11/2005 | Gunaratnam et al. |
| 2005/0257686 A1* | 11/2005 | Occhialini ......... B01D 53/0476 95/96 |
| 2006/0266361 A1 | 11/2006 | Hernandez |
| 2009/0044808 A1 | 2/2009 | Guney et al. |
| 2009/0101154 A1 | 4/2009 | Mutti et al. |
| 2009/0320851 A1 | 12/2009 | Selvarajan et al. |
| 2010/0043801 A1 | 2/2010 | Halling et al. |
| 2010/0116270 A1 | 5/2010 | Edwards et al. |
| 2010/0252037 A1 | 10/2010 | Wondka et al. |
| 2010/0252039 A1 | 10/2010 | Cipollone et al. |
| 2011/0240035 A1 | 10/2011 | Gillies |
| 2012/0055482 A1 | 3/2012 | Wilkinson |
| 2012/0167888 A1 | 7/2012 | Taylor et al. |
| 2012/0204870 A1 | 8/2012 | McAuley et al. |
| 2015/0250973 A1 | 9/2015 | Allum et al. |
| 2015/0314098 A1 | 11/2015 | Allum et al. |
| 2016/0279362 A1 | 9/2016 | DeVries et al. |
| 2017/0072159 A1* | 3/2017 | Romano ........... A61M 16/0003 |

FOREIGN PATENT DOCUMENTS

| | | |
|---|---|---|
| CN | 102159273 A | 8/2011 |
| CN | 101405047 | 5/2012 |
| CN | 101455871 | 1/2016 |
| EP | 1849491 A1 | 10/2007 |
| EP | 2347781 A1 | 7/2011 |
| WO | WO 2010/115166 | 10/2010 |
| WO | WO 2010/115168 | 10/2010 |
| WO | WO 2010/115169 | 10/2010 |
| WO | WO 2010/115170 | 10/2010 |
| WO | WO 2011/029073 | 3/2011 |
| WO | WO 2011/029074 | 3/2011 |
| WO | WO 2012/063532 A1 | 5/2012 |
| WO | WO 2012/177566 A1 | 12/2012 |

OTHER PUBLICATIONS

Search Report and Written Opinion received in International Application No. PCT/US2020/015103, dated Mar. 24, 2020.
Extended European Search Report for Application No. 13837336.0 dated Mar. 21, 2016.
Final Office Action received for U.S. Appl. No. 14/427,986 dated Nov. 26, 2048, 12 pages.
Non Final Office Action received for U.S. Appl. No. 14/427,986 dated May 30, 2018, 20 pages.
Non Final Office Action received for U.S. Appl. No. 14/427,986 dated Oct. 19, 2017, 31 pages.
Notice of Allowance received for U.S. Appl. No. 14/427,986 dated Feb. 11, 2019, 8 pages.
Notice of Allowance received for U.S. Appl. No. 14/427,986 dated May 16, 2019, 13 pages.
Nasal Interface Apparatus and Systems for Use With a Respiratory Assist Device, U.S. Appl. No. 16/275,255, 2019/0175860 A1.
Nasal Interface Apparatus and Systems for Use With a Respiratory Assist Device U.S. Appl. No. 14/427,986, U.S. Pat. No. 10,384,028.

* cited by examiner

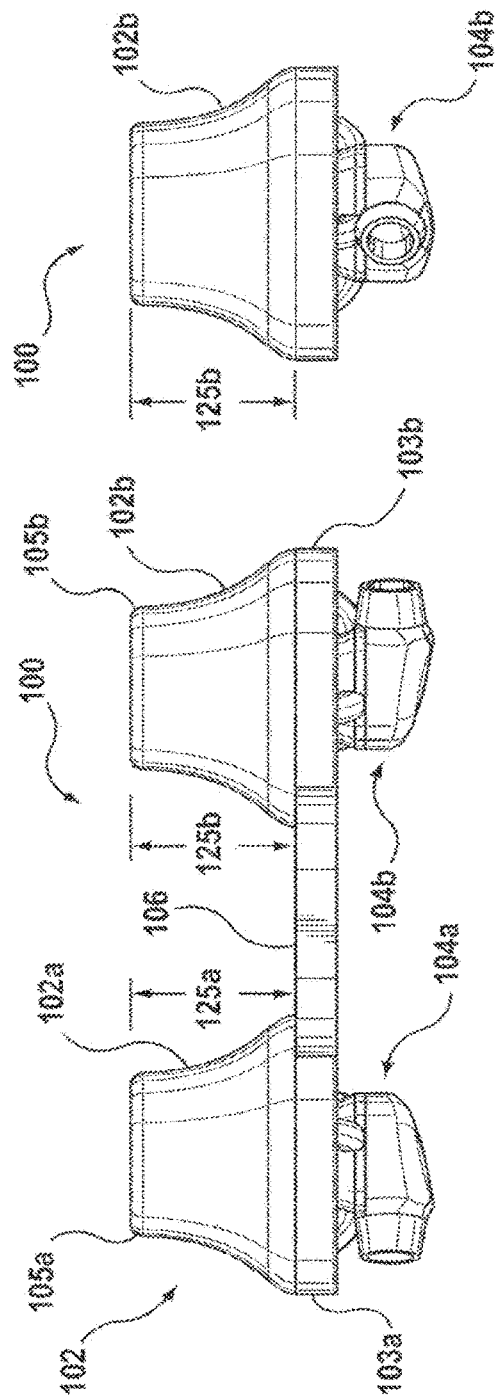
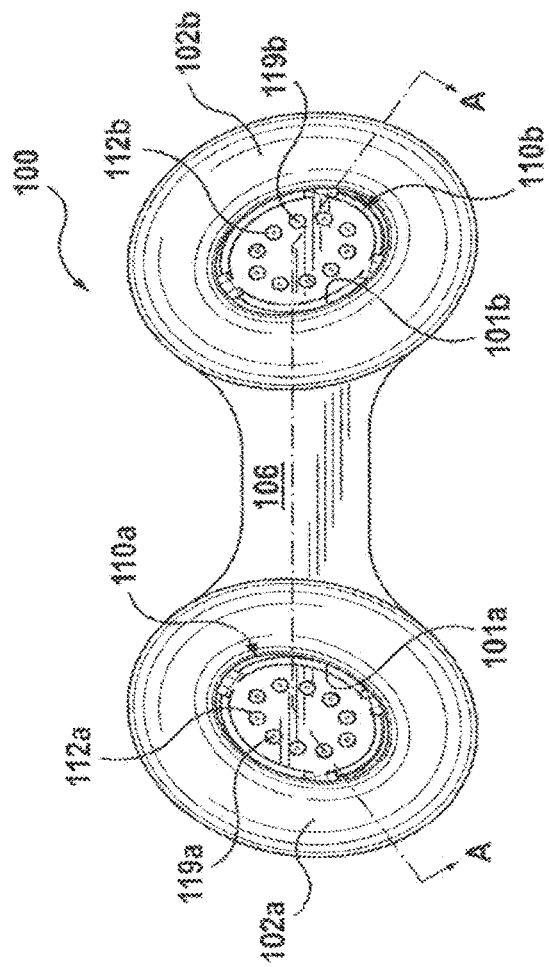

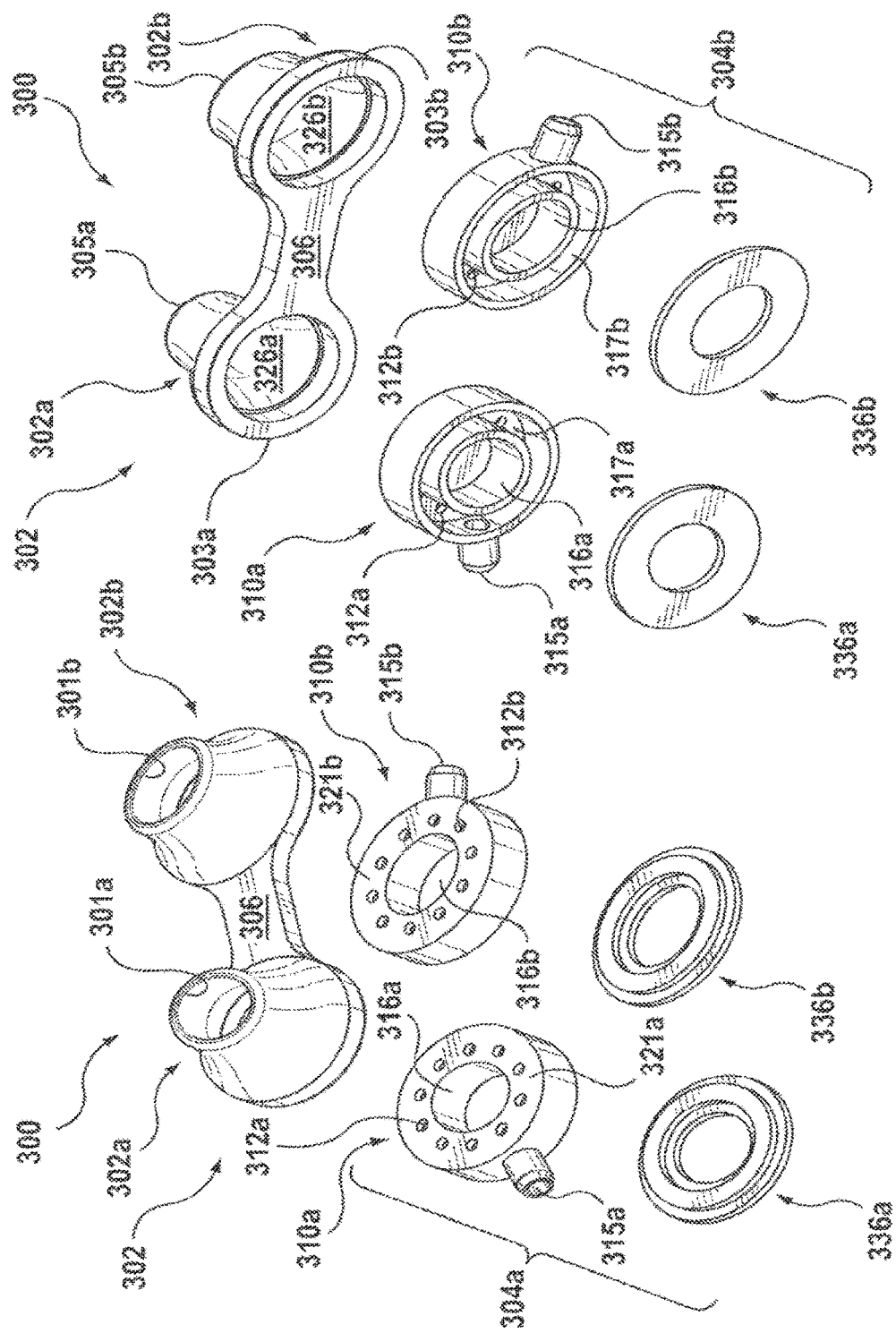

NASAL INTERFACE APPARATUS AND SYSTEMS FOR USE WITH A RESPIRATORY ASSIST DEVICE

CROSS-REFERENCE TO RELATED APPLICATIONS

This application is a continuation-in-part of U.S. patent application titled, "NASAL INTERFACE APPARATUS AND SYSTEMS FOR USE WITH A RESPIRATORY ASSIST DEVICE," filed on Feb. 13, 2019 and having application Ser. No. 16/275,255, which is a continuation of U.S. patent application titled, "NASAL INTERFACE APPARATUS AND SYSTEMS FOR USE WITH A RESPIRATORY ASSIST DEVICE," filed on Mar. 12, 2015 and having application Ser. No. 14/427,986, now U.S. Pat. No. 10,384,028, which is a national phase application of the international application titled, "NASAL INTERFACE APPARATUS AND SYSTEMS FOR USE WITH A RESPIRATORY ASSIST DEVICE," filed Aug. 27, 2013 and having Application No. PCT/US2013/056702, which claims the priority benefit of the U.S. Provisional Patent application having Application No. 61/699,969, filed Sep. 12, 2012. The subject matter of these related applications is hereby incorporated herein by reference. This application also claims the priority benefit of the U.S. Provisional Patent application having Application No. 62/796,563, filed Jan. 24, 2019 and titled "DESIGNS FOR MECHANICAL VENTILATION", which is hereby incorporated by reference in its entirety.

FIELD OF THE INVENTION

The invention is directed to the delivery of a respiratory gas to assist the spontaneous breathing effort of a patient with a breathing disorder, and more particularly to ambulatory nasal interface apparatus and systems for delivering the respiratory gas to the patient.

BACKGROUND OF THE INVENTION

There is a need for a minimally obtrusive nasal interface, patient circuit tubing and ventilation system that delivers mechanical ventilatory support or positive airway pressure, while minimizing exhalation resistance and permitting less encumbered movement and/or ambulation of a patient so as to facilitate mobility of the patient and/or to allow activities of daily living. There are a range of clinical syndromes that require ventilation therapy that would benefit from such an interface and system, such as respiratory insufficiency, chronic obstructive lung or pulmonary disease (most commonly referred to as COPD), interstitial lung disease, fibrosis, acute respiratory distress syndrome (ARDS), airway or sleep disordered breathing, congestive heart failure and neuromuscular impairment.

There are two general types of mechanical ventilation (MV) modes. A first type delivers gas to a patient based on a frequency selected by the clinician which is independent of patient activity. This type of ventilation, known as controlled mechanical ventilation, is used when the ventilator is needed to breathe for the patient such as when the patient is non-alert, sedated, unresponsive or paralyzed. A second type of ventilation, known as assisted mechanical ventilation, or assisted ventilation, delivers gas to the patient in response to an inspiratory effort generated by the patient. This type of ventilation helps the patient breathe, such as when the patient has respiratory insufficiency and/or dyspnea associated with COPD. There are also ventilators and modes of ventilation that combine the two modes of ventilation described above.

Certain invasive MV therapies connect to the patient by intubating the patient with a endotracheal tube, which is a tube inserted in the patient's mouth that extends to their voice box, or with a cuffed or uncuffed tracheal tube, which is a tube inserted through a stoma in the patient's throat area. While helpful in supporting the work of breathing, the patient interfaces used for invasive MV are obtrusive and/or invasive to the user, and obviously would not facilitate mobility or activities of daily living of the patient. Non-invasive mechanical ventilation (NIV) therapies also are known that ventilate a patient with a face or nasal mask rather than requiring intubation or tracheal tube. However, known non-invasive face or nasal masks are bulky and cumbersome and require a patient circuit with large diameter tubing that restricts movement and is also bulky and cumbersome. The non-invasive nasal masks used in these forms of mechanical ventilation operate using a closed gas circuit. A closed circuit system requires the mask to create a gas/air seal against the nose and/or mouth which can be uncomfortable to the patient. The bulky nature of known masks and patient circuits create a 'dead space' in the hollow areas of the mask and patient circuit. This dead space, coupled with the requirement of a closed system result in carbon dioxide ($CO_2$) accumulating in the 'dead space' or hollow areas of the mask and patient circuit. The accumulation of $CO_2$ needs to be flushed out of the patient circuit or mask to avoid the problem of the patient re-breathing $CO_2$. The $CO_2$ is flushed out the dead space by maintaining a constant low flow in the ventilator, mask and patient circuit system which creates a positive pressure at the patient connection port. This pressure creates exhalation resistance that is sometimes uncomfortable to the patient. Also, closed circuit ventilation systems increase the risk of the ventilator over pressurizing the patient's lungs, which can result in trauma to the airway tissues and then longer-term patient ventilator dependency. Consequently, known invasive and non-invasive mechanical ventilation systems do not facilitate activities of daily living of the patient or mobility due to their bulky nature, and present risks of trauma to the patient's lungs due to the closed circuit breathing tubes.

For treating sleep disorders such as sleep disordered breathing (SDB), the preferred ventilation therapies are continuous positive airway pressure (CPAP) and bi-level positive airway pressure (BiPAP). CPAP and BiPAP are a variant of mechanical non-invasive ventilation. Positive pressure applied by the ventilator in the form of CPAP or BiPAP is connected to the patient by a nasal or face mask that seals against the nose or face. The seal allows CPAP and BiPAP to operate as a closed circuit ventilation system and to treat sleep disordered breathing by pressurizing the upper airways and thereby preventing upper airway obstruction. While effective, this therapy has poor patient compliance because the patient interface and corresponding patient circuit tubing is obtrusive to the patient. As with mechanical invasive and non-invasive ventilation, the bulky nature of the CPAP and BiPAP masks and patient circuits create a 'dead space' in the hollow areas of the mask and patient circuit. This dead space, coupled with the requirement of a closed system result in $CO_2$ accumulating in the 'dead space' or hollow areas of the mask and patient circuit. The accumulation of $CO_2$ needs to be flushed out of the patient circuit or mask to avoid the problem of the patient re-breathing $CO_2$. The $CO_2$ is flushed out of the dead space by maintaining a constant low flow in the ventilator, mask and patient circuit system which creates a positive pressure at the patient connection port. This constant pressure creates exhalation resistance that is sometimes uncomfortable to the patient. Also, the closed circuit ventilation systems, such as CPAP and BiPAP, require the patient, in most instances, to unnaturally breathe through both a mask and gas delivery circuit, which can be uncomfortable.

Oxygen therapies are categorically different and distinct from mechanical ventilation therapies. Oxygen therapy increases the concentration of oxygen in the patient's lungs, blood oxygen saturation levels and increases oxygen availability to other organs, which can increase lifespan of patients suffering from the above noted syndromes. While oxygen therapy has been demonstrated to improve lifespan, there is a lack of evidence demonstrating that oxygen therapy can reduce the severe feelings of breathlessness, work of breathing and discomfort a patient experiences resulting from the above noted syndromes. Consequently, oxygen therapies, e.g., continuous flow and pulsed flow, are used for far less severe forms of the noted syndromes than mechanical ventilation therapies. Oxygen therapies work by utilizing nasal cannulas or masks to deliver concentrated oxygen to the patient. Concentrated oxygen is delivered to the patient in a 'continuous' flow rate that is provided during the patient's inspiratory and expiratory breathing cycles, using a set continuous liter per minute (LPM) flow of oxygen. Also, concentrated oxygen is delivered to the patient in an 'intermittent' flow rate using oxygen therapy devices known as oxygen conservers. Oxygen conserver devices deliver an intermittent flow of oxygen only during the patient's inspiratory breathing cycle. Mechanical ventilation therapy, on the other hand, has decades of well-established evidence demonstrating a significant reduction in breathlessness, work of breathing, and discomfort experienced by patients that suffer from the above noted syndromes. Mechanical ventilation therapies can both utilize concentrated oxygen to improve lifespan and provide mechanical breathing support to improve breathing function, i.e., reduce breathlessness, work of breathing and patient discomfort. Correspondingly, mechanical ventilation therapy is different than oxygen therapy and therefore is used to treat patient populations with more severe forms of the above noted syndromes.

One or more of the above-identified disadvantages of known therapies has been attempted to be solved by a non-invasive open ventilation (NIOV) system recently developed by Breathe Technologies, Inc. of Irvine, Calif. that is used with bottled oxygen to deliver augmented $O_2$ tidal volume and entrained air during a patient's spontaneous breathing so as to deliver both ventilation and supplemental oxygen with every breath. This volume augmentation is provided via a nasal pillow interface having entrainment ports that are open to ambient air. Generally the system senses the patient's spontaneous breath through a sense port in the nasal interface, and then delivers the selected pressurized volume of oxygen. As oxygen is delivered, ambient air is entrained through the entrainment ports, and positive pressure is developed within the interface to supplement the patient's spontaneous breathing. Although the NIOV system facilitates mobility and activities of daily living, the nasal pillow interface is bulky. It circumferentially extends from below the patient's nose to partially circumscribe the patient's face on either side thereof in order to have a length that can accommodate a throat area of the interface, which is necessary to develop positive pressure within the interface prior to delivery of the air oxygen mixture to the patient. This throat area that circumscribes the patient's face also creates a 'dead space' in the hollow areas of the nasal pillow interface. In addition, the nasal interface tubing includes a first lumen for sensing the patient's breathing effort and a second lumen for delivering a pressurized volume of oxygen to the patient. Consequently, a diameter of tubing used with the nasal interface and patient circuit must have an overall larger outer diameter to accommodate the requirement of distinct sensing and delivery lumens. Thus when worn by the patient, the overall size and weight of the nasal interface and patient circuit tubing associated therewith is not insubstantial and may even be considered by some patients as cumbersome and/or burdensome.

Accordingly, there still exists a need in the art for minimally obtrusive nasal interfaces and patient circuits that deliver mechanical ventilatory support or positive airway pressure, while permitting less encumbered movement so as to facilitate mobility of the patient and to allow activities of daily living. Embodiments hereof are directed to a low profile and light weight nasal interface that is configured to provide improved entrainment of ambient air so as to conserve the amount of compressed respiratory gas used by a patient while providing increased ventilatory support and/or positive airway pressure.

BRIEF SUMMARY OF THE INVENTION

An ambulatory assist ventilation (AAV) apparatus and system are disclosed for the delivery of a respiratory gas to assist the spontaneous breathing effort of a patient with a breathing disorder. The AAV system includes a compressed respiratory gas source, a respiratory assist device for controlling respiratory gas flow, and a low profile open nasal interface device, which does not have a dead space or hollow area where $CO_2$ can collect, and patient circuit tubing for delivering the respiratory gas to the patient, wherein the nasal interface device is fluidly connected to the respiratory assist device via tubing for receiving the respiratory gas therefrom. The nasal interface device operates under the Venturi principle by utilizing the energy of the delivered respiratory gas to entrain ambient air and increase airway pressure thereby increasing the net volume delivered to the patient. Embodiments of nasal interface device disclosed herein are configured in an open, compact, low profile manner, which does not have a dead space or hollow area where $CO_2$ can collect, and are significantly smaller, lighter in weight and higher performing as compared to known breathing masks.

In one embodiment, a non-invasive air entrainment and portable oxygen concentrator system is provided. The system includes a small, lightweight nasal pillow and a lightweight, portable oxygen concentrator tuned to work with the nasal pillow to augment the tidal volume of the patient. The nasal pillow is configured to entrain ambient air in the oxygen enriched gas from the oxygen concentrator to increase the tidal volume without requiring any invasive mechanical ventilation. The oxygen concentrator is lightweight, in some embodiments weighing less than 9 lbs, and yet tuned to provide sufficient flow rate for the nasal pillow to increase the inspiratory flow rate to a level required by the patient. In some implementations, the augmented inspiratory flow rate can be 100 LPM or higher. In some implementations, the system is adaptive in that the augmented inspiratory flow rate can be adjusted based on patient requirement.

In one embodiment, a system for providing oxygen and mechanical ventilation therapy including a nasal interface apparatus for use with a respiratory device that provides gas from a gas source is provided. The system comprises: a pair of hub components for receiving the compressed gas with each hub component having a plurality of delivery openings in a distal face thereof; and a pair of nasal pillows, each nasal pillow extending from a proximal end to a distal end thereof, wherein each nasal pillow has a respective hub component disposed at the proximal end of the nasal pillow such that the plurality of delivery openings of the hub component are positioned to deliver the compressed gas into the nasal pillow; characterized by: the gas source is a portable oxygen concentrator, weighing less than 11 pounds; the nasal interface apparatus is connected to a portable oxygen concentrator output; the total gas flow output, including concentrated oxygen, of the concentrator in combination with the air entrained by the nasal interface provides simultaneous ambulatory oxygen and mechanical ventilation therapy to a patient wearing the nasal interface. In some implementations, the flow amplification rate due to entrainment is 5 times. In some implementations, the portable oxygen concentrator peak oxygen flowrate output is between 10 and 20 Liters Per Minute (LPM) when delivered synchronously with the onset of the patient's inspiration. In some implementations, the portable oxygen concentrator peak oxygen flowrate output is greater than 20 LPM when delivered synchronously with the onset of the patient's inspiration. In some implementations, the portable oxygen concentrator total gas flow output is 16 LPM per liter of oxygen produced or less and the portable oxygen concentrator weighs 5.4 pounds or less per liter of oxygen produced. In some implementations, the portable oxygen concentrator gas flowrate output is 20 LPM or less per liter of oxygen produced and the portable oxygen concentrator weighs 6.75 pounds or less per liter of oxygen produced.

In other embodiments, a non-invasive air entrainment device in the form of a nasal interface device may be used in combination with other gas sources, such as oxygen concentrators to provide dual therapy capability suitable for some applications.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a nasal interface device in accordance with an embodiment hereof.

FIG. 2 is an end view of the nasal interface device of FIG. 1.

FIG. 3 is a top view of the nasal interface device of FIG. 1.

FIGS. 17 and 18 are exploded perspective views of the nasal interface device of FIG. 16 showing various subcomponents thereof.

DETAILED DESCRIPTION OF THE INVENTION

Specific embodiments of the present invention are now described with reference to the figures, wherein like reference numbers indicate identical or functionally similar elements. The terms "proximal" and "distal" are used in the following description with respect to a position or direction relative to the respiratory assist device. "Proximal" and "proximally" are a position near from or in a direction toward the respiratory assist device. "Distal" or "distally" are a position distant or in a direction away from the respiratory assist device.

The following detailed description is merely exemplary in nature and is not intended to limit the invention or the application and uses of the invention. Although the descriptions of embodiments hereof are in the context of treatment of a range of clinical syndromes that require respiratory assistance, the invention may also be used in any other therapies and/or situations where it is deemed useful. Furthermore, there is no intention to be bound by any expressed or implied theory presented in the preceding technical field, background, brief summary or the following detailed description.

Figure 4:
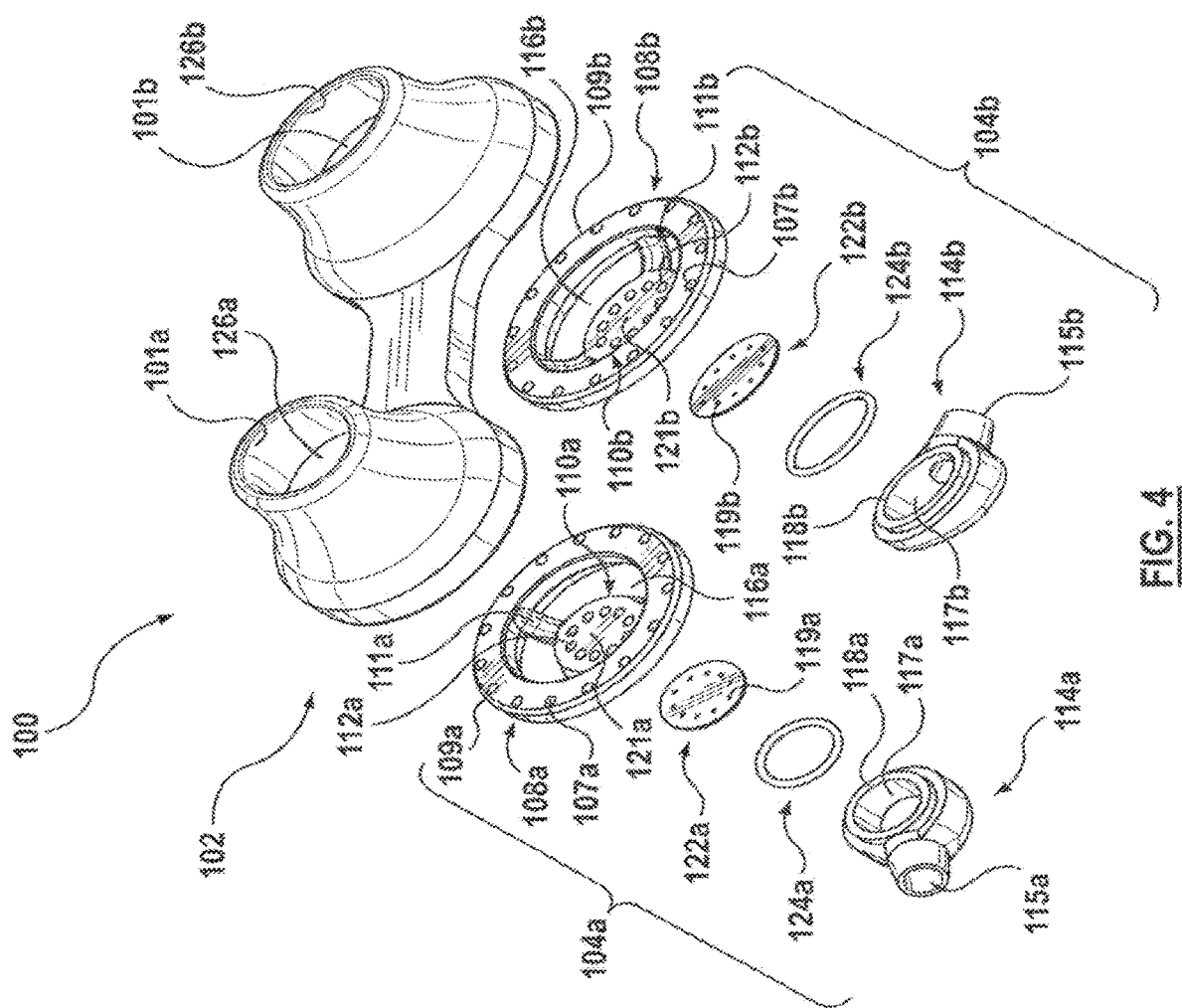
FIGS. 4 and 5 are exploded perspective views of the nasal interface device of FIG. 1 showing various subcomponents thereof.
Figure 5:
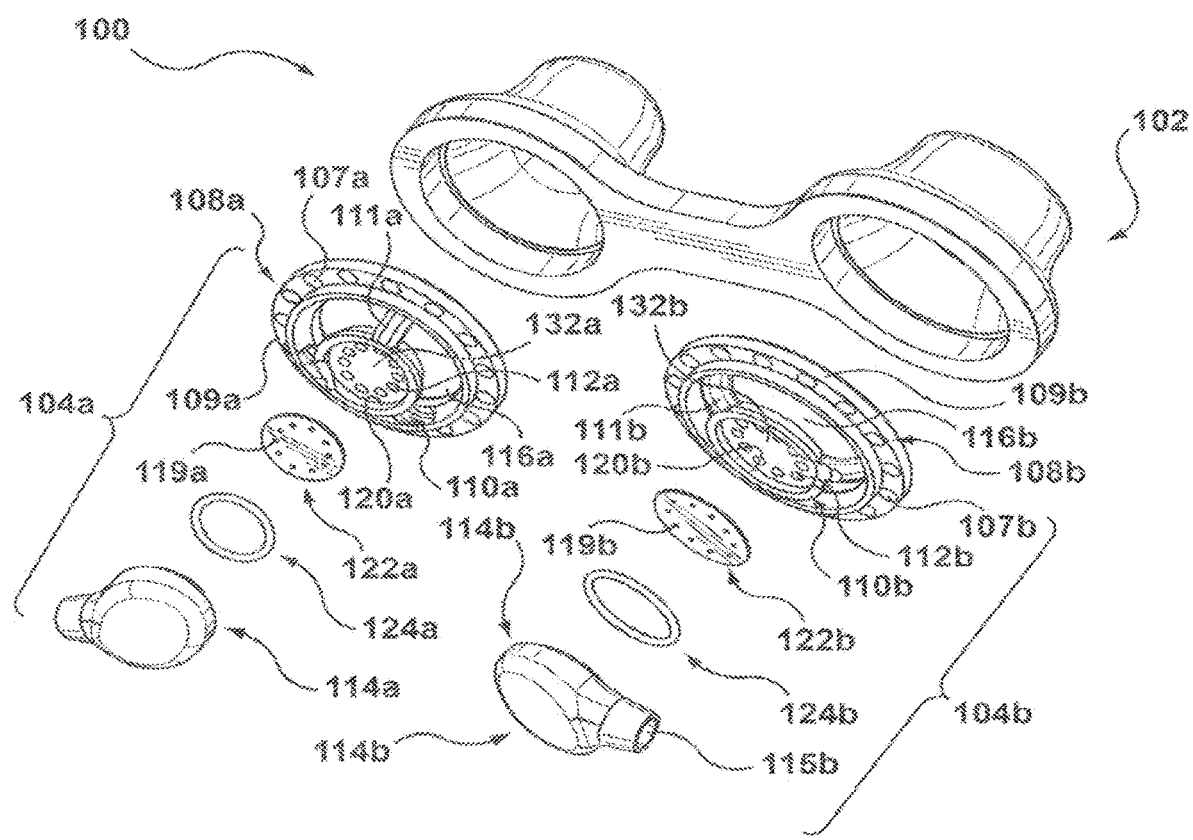
Figure 6:
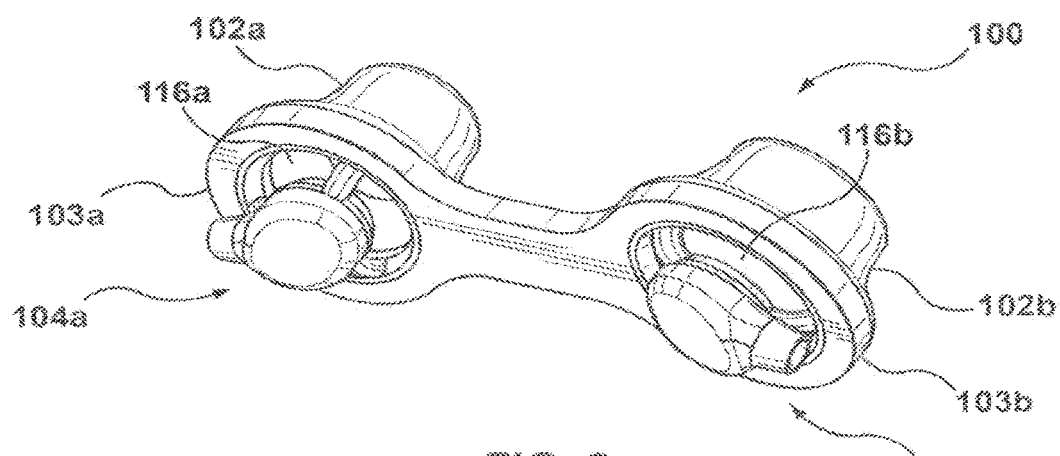
FIG. 6 is a perspective bottom view of the nasal interface device of FIG. 1.
Figure 7:
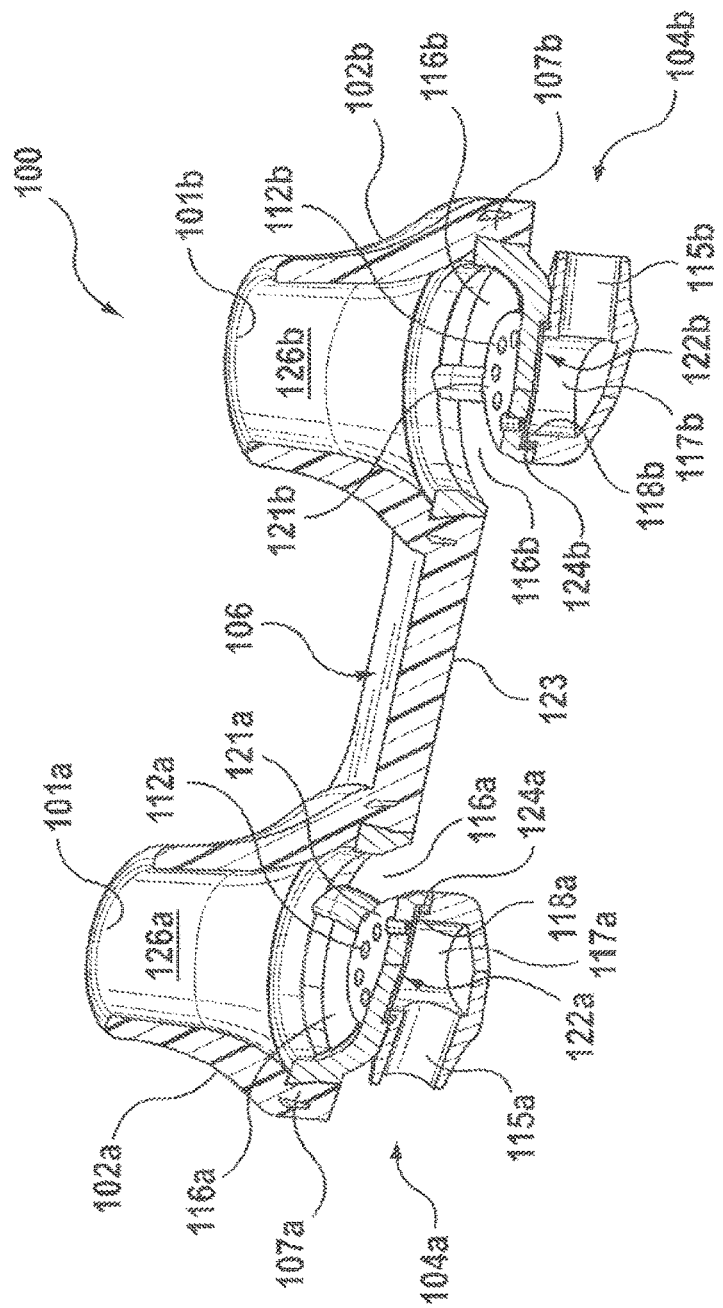
FIG. 7 is a sectional view of the nasal interface device of FIG. 3 taken along line A-A thereof.

FIGS. 1-7 depict various views of a nasal interface device 100 in accordance with an embodiment hereof. FIGS. 1, 2 and 3 are side, end and top views, respectively, of nasal interface 100 with FIGS. 4 and 5 being exploded perspective views of nasal interface 100 that show the various components thereof. FIG. 6 is a perspective bottom view of nasal interface 100, whereas FIG. 7 is a sectional view of nasal interface 100 taken along line A-A of FIG. 3.

Nasal interface 100 is used with a respiratory assist device that doses compressed respiratory gas from a compressed respiratory gas source, as will be described in more detail below. Generally, nasal interface 100 is configured to be worn by a user to deliver a mixture of respiratory gas and entrained ambient air during an inspiratory effort of the patient and to permit exhalation therethrough during an expiratory effort of the patient, which will also be described in more detail below.

Nasal interface 100 includes a nasal pillow component 102 and a pair of hub components 104a, 104b. Nasal pillow component 102 includes nasal pillows 102a, 102b that are tubular structures with proximal or first ends 103a, 103b and distal or second ends 105a, 105b. A central passageway 126a, 126b is defined by tubular body portions 125a, 125b of each nasal pillow 102a, 102b from substantially a first end 103a, 103b to a respective second end 105a, 105b thereof. In embodiments hereof, at least each of tubular body portions 125a, 125b of nasal pillows 102a, 102b is configured to have an ergonomic oval cross-section along an entire length thereof and are intended to be inserted in their entirety into the nasal cavity to assist in anchoring nasal interface 100 within a user's nostrils. A connector strip 106 is a thin flexible segment of nasal pillow component 102 that extends between first ends 103a, 103b of nasal pillows 102a, 102b, respectively, to provide flexibility and articulation between nasal pillows 102a, 102b so as to permit adjustment to the particular anatomy of a user. In embodiments hereof, connector strip 106 may be a sinusoidal strip, two or more, parallel strips, or a chain or series of oval or circular shapes that extend between nasal pillows 102a, 102b, respectively. In an embodiment, nasal pillow component 102 with nasal pillows 102a, 102b and connector strip 106 is a molded component of an elastomeric material, such as 30 Shore A silicone. The pillows do not require or include a "bulge" or shock absorber section that are typically found in the art to permit the pillows to articulate and compress to fit and seal against the anatomy of a user because the connector strip 106, allows the nasal pillow components to independently articulate in order for them to fit entirely into the user's nostrils creating an airtight seal.

Hub components 104a, 104b are concentrically disposed with first ends 103a, 103b of nasal pillows 102a, 102b, respectively. With reference to the exploded views of nasal interface 100 depicted in FIGS. 4 and 5, each hub component 104a, 104b includes a distal support structure 108a, 108b, a central hub 110a, 110b with a plurality of delivery openings 112a, 112b, and a proximal plenum structure 114a, 114b. The plurality of delivery openings 112a, 112b of each hub component 104a, 104b are periodically spaced about a perimeter of a distal face 121a, 121b of respective central hub 110a, 110b. In an embodiment, each delivery opening 112a, 112b has a substantially circular cross-section. Proximal plenum structures 114a, 114b in conjunction with central hub 110a, 110b form an enclosed space or plenum in which the air pressure is elevated above ambient pressure. Distal support structures 108a, 108b include annular rims 109a, 109b and spokes or struts 111a, 111b that radially extend between annular rims 109a, 109b and respective central hubs 110a, 110b. Although shown with three spokes 111a, 111b, more or fewer spokes may be used in support structures 108a, 108b in accordance with various embodiments hereof. In an embodiment, each support structure 108a, 108b and its respective central hub 110a, 110b is a single molded component of a polycarbonate. A series of ambient air apertures 116a, 116b are formed between respective annular rims 109a, 109b, adjacent spokes 111a, 111b and central hubs 110a, 110b, such that as shown in FIGS. 6 and 7, the series of ambient air apertures 116a, 116b of nasal interface 100 are disposed proximate first ends 103a, 103b of each nasal pillow 102a, 102b, respectively, to substantially surround the respective central hub 110a, 110b disposed therein.

Central hubs 110a, 110b of hub components 104a, 104b are positioned to be coaxial with respective distal ports 101a, 101b of nasal pillows 102a, 102b such that the plurality of delivery openings 112a, 112b of each hub are positioned to deliver a respiratory gas within its respective nasal pillow. Proximal plenum structures 114a, 114b of hub components 104a, 104b define an inlet 115a, 115b for receiving a respiratory gas from the respiratory assist device (not shown) and a plenum or chamber 117a, 117b for distributing the respiratory gas to the plurality of delivery openings 112a, 112b of respective central hubs 110a, 110b. Proximal plenum structures 114a, 114b include distally extending annular flanges 118a, 118b that snap, or are otherwise secured by ultrasonically welding or gluing, within corresponding proximal recesses 120a, 120b within central hubs 110a, 110b. In an embodiment, plenum structures 114a, 114b are molded components of a polycarbonate or acrylonitrile butadiene styrene (ABS).

Hub components 104a, 104b further include outlet discs 122a, 122b having a plurality of outlets or holes 119a, 119b and seals 124a, 124b. In an embodiment, outlet discs 122a, 122b are formed from a thin sheet of a metal, such as stainless steel or brass, with outlets 119a, 119b formed therethrough by electrochemical etching. In an embodiment, outlet discs 122a, 122b have a thickness or depth of less than 0.040 inch with each outlet 119a, 119b having a diameter of less than 0.010 inch. In another embodiment, outlet discs 122a, 122b have a thickness or depth that is less than a diameter of each outlet 119a, 119b, e.g., an outlet disc thickness or depth of 0.005 inch and an outlet diameter of 0.010 inch. The plurality of outlets 119a, 119b of outlet discs 122a, 122b correspond in number and orientation to the plurality of delivery openings 112a, 112b of respective central hubs 110a, 110b. In an embodiment, each of the delivery openings 112a, 112b has a diameter that is slightly greater than the diameter of a corresponding disc outlet with each delivery opening 112a, 112b being sized to be large enough to not impede on the flow exiting from a corresponding disc outlet 119a, 119b. Outlet discs 122a, 122b and seals 124a, 124b are disposed within proximal recesses 120a, 120b of central hubs 110a, 110b such that disc outlets 119a, 119b substantially align with corresponding central hub delivery openings 112a, 112b. The configuration of each disc outlet 119a, 119b, i.e., diameter and depth, and respective larger hub delivery opening 112a, 112b provides for a softer more diffusive gas flow to the patient such that the patient is less likely to experience discomfort due to flow impingement, most particularly if the disc outlet thickness or depth is less than a diameter of the disc outlet. In the embodiment of FIGS. 1-7, outlet discs 122a, 122b and central hubs 110a, 110b are oval. In order to assure alignment of disc outlets 119a, 119b and delivery openings 112a, 112b, outlet discs 122a, 122b are held or pressed against respective proximal faces 132a, 132b of central hubs 110a, 110b by respective annular flanges 118a, 118b of proximal plenum structures 114a, 114b with seals 124a, 124b therebetween.

Hub components 104a, 104b, as described above, are attached to nasal pillow component 102 by respective annular rims 109a, 109b, each of which in the embodiment shown in FIGS. 4 and 5 includes a series of post-forming apertures 107a, 107b that receive a material of nasal pillow component 102 there through in an over-molding process that is used to connect the structures together, as best seen in the sectional view of nasal interface 100 shown in FIG. 7. In another embodiment, nasal pillow component 102 may be glued or otherwise attached to annular rims 109a, 109b of hub components 104a, 104b.

Figure 10:
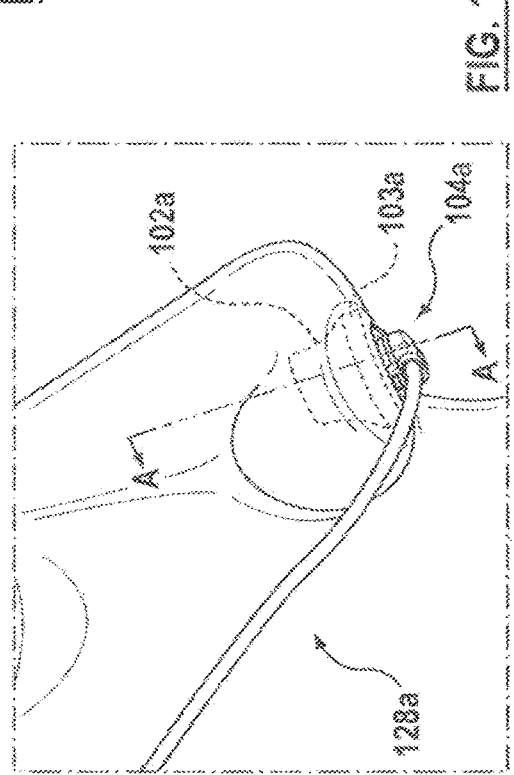
FIG. 10 is a side view depiction of the nasal interface apparatus as shown in FIG. 8 being worn by a patient.
Figure 10A:
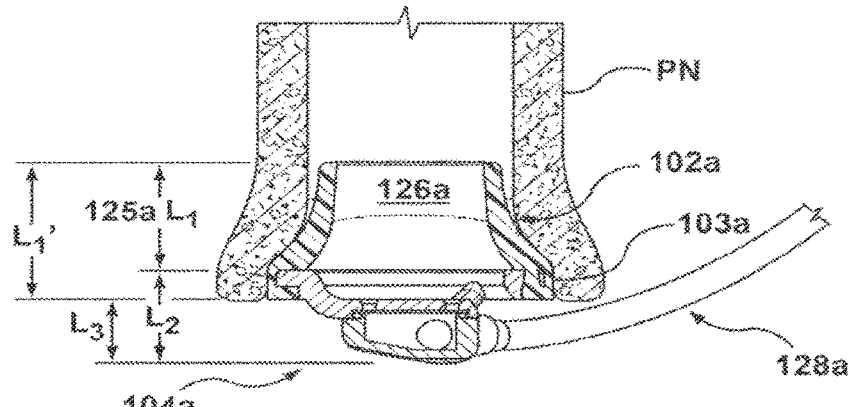
FIG. 10A is a sectional view of a portion of the nasal interface apparatus within a patient's nostril as shown in FIG. 10 taken along line A-A thereof.
Figure 10B:
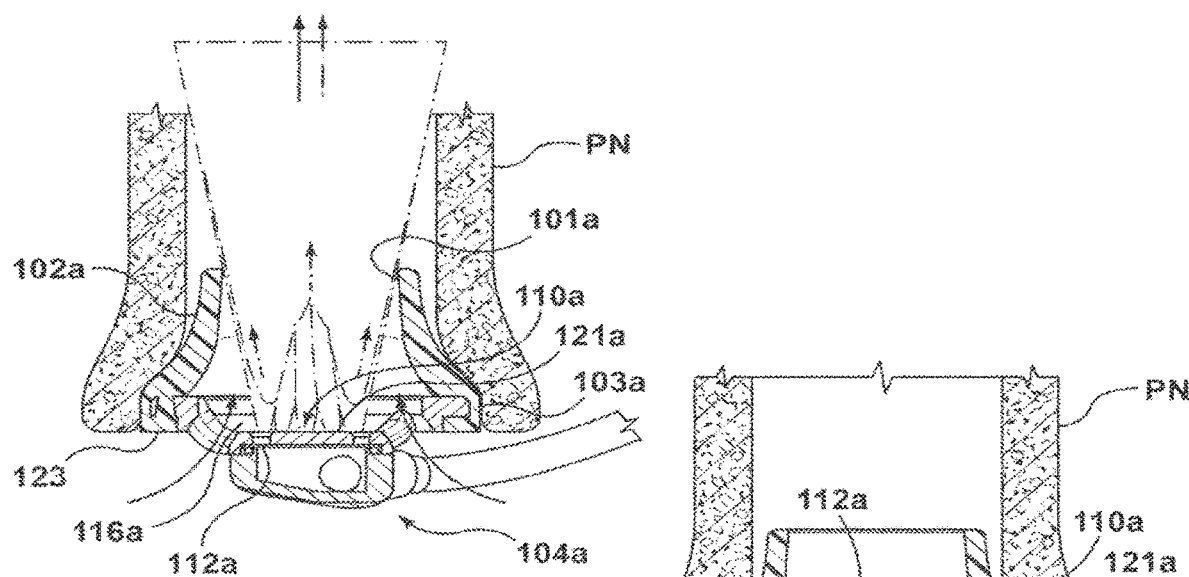
FIG. 10B is the sectional view of the portion of the nasal interface apparatus shown in FIG. 10A depicting the delivery of a respiratory gas during an inspiratory effort of the patient.
Figure 10C:
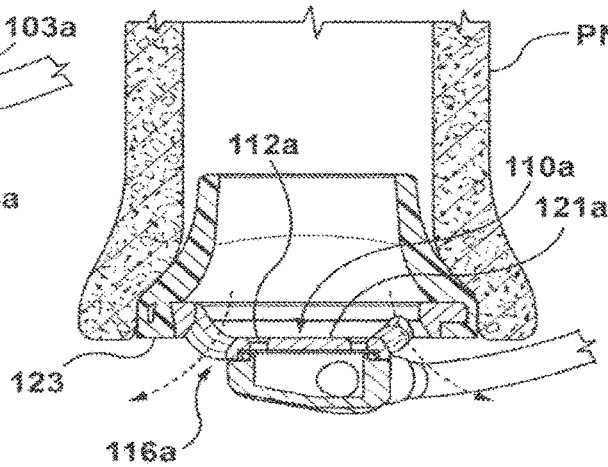
FIG. 10C is the sectional view of the portion of the nasal interface apparatus shown in FIG. 10A depicting an expiratory effort of the patient.

As shown in FIG. 3, a pattern of the plurality of disc outlets 119a, 119b and delivery openings 112a, 112b of central hubs 110a, 110b, respectively, are shaped and positioned to correspond with the respective distal port 101a, 101b of nasal pillows 102a, 102b so that the flow of a respiratory gas from the plurality of disc outlets 119a, 119b and delivery openings 112a, 112b in conjunction with ambient air that is entrained by the respiratory gas flow from ambient air apertures 116a, 116b substantially fills the respective proximal port 101a, 101b prior to entering a respective nare of the patient, which will be explained in more detail below with reference to FIGS. 10A through 10C. In the embodiment of FIG. 3, the plurality of disc outlets 119a, 119b and delivery openings 112a, 112b are in a pattern that corresponds to a shape of the respective proximal port 101a, 101b of nasal pillows 102a, 102b. In various other embodiments, the plurality of disc outlets 119a, 119b and delivery openings 112a, 112b may be arranged to form, for example, a circular, polygonal or cross pattern or a series of parallel lines through a respective central hub 110a, 110b that is configured such that the respective nasal pillow proximal port 101a, 101b is filled with the respiratory gas/ambient air outflow stream that is created thereby. In various embodiments hereof, an outlet disc may be omitted with the plurality of delivery openings of the central hubs being sized and configured to produce/deliver the pressurized respiratory gas/entrained air outflow stream to the respective nasal pillow proximal ports.

Figure 8:
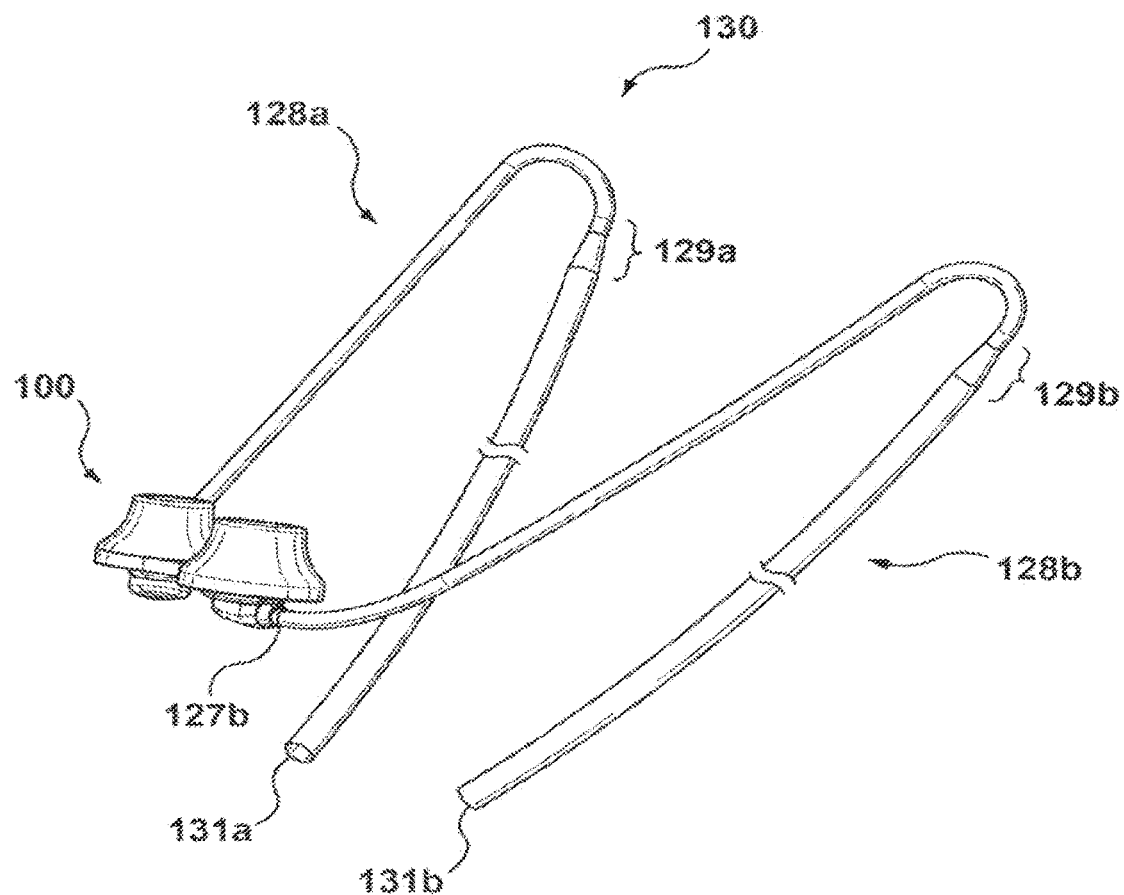
FIG. 8 is a perspective view of a nasal interface apparatus that depicts the nasal interface device of FIG. 1 connected to tubing for fluidly coupling to a respiratory assist device (not shown) and a pressurized respiratory gas source (not shown).
Figure 9:
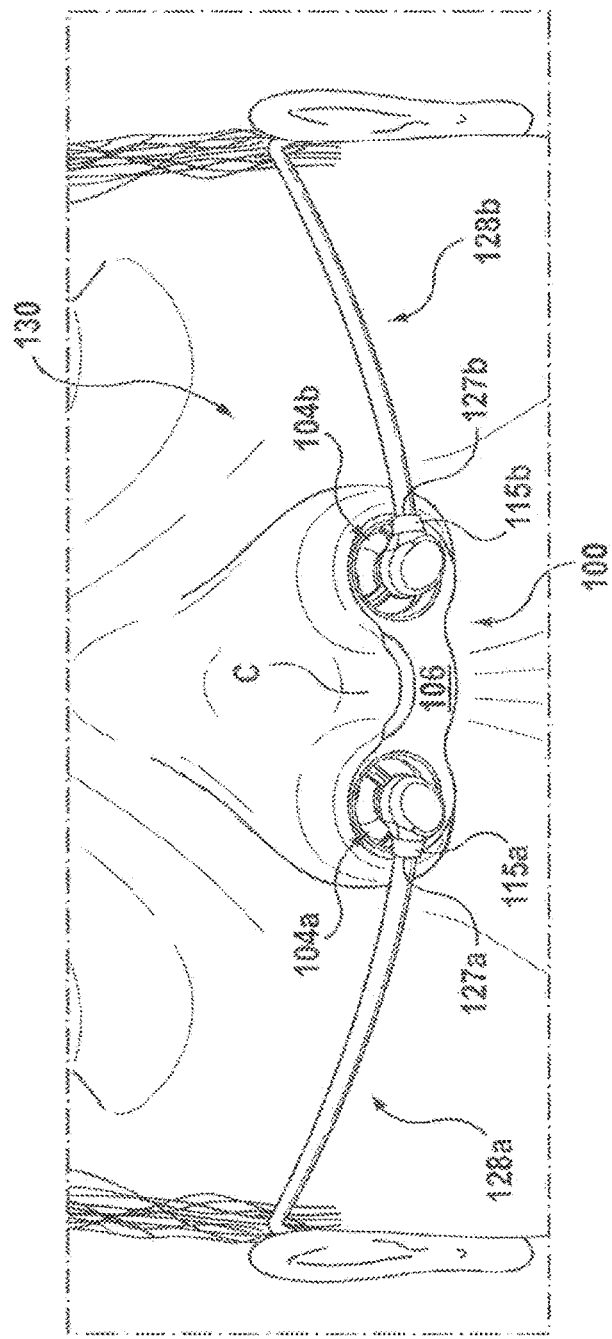
FIG. 9 is a frontal view depiction of the nasal interface apparatus as shown in FIG. 8 being worn by a patient.

FIG. 8 is a perspective view of a nasal interface apparatus 130 that includes nasal interface 100 connected to tubing or tubes 128a, 128b for fluidly coupling the nasal interface to a respiratory assist device (not shown) and a pressurized respiratory gas source (not shown), with FIGS. 9 and 10 being frontal and side views, respectively, depicting nasal interface apparatus 130 being worn by a patient. The unencumbering, low profile of nasal interface 100 is clearly depicted in FIGS. 9 and 10 and the minimal diameter and substantially 90.degree. approach of tubing 128a, 128b into inlets 115a, 115b of hub components 104a, 104b adds to the overall unencumbering nature of nasal interface apparatus 130, which may help to reduce the self-consciousness of a wearer, to reduce impediment while eating and drinking, and/or to reduce interference with eye wear and facial hair, such as mustaches. Tubing 128a, 128b includes a first inner diameter from first or distal ends 127a, 127b, where each of tubing 128a, 128b connects with the respective hub component inlet 115a, 115b, to flared or stepped-up segments 129a, 129b of tubing 128a, 128b that are disposed along a length of the respective tubing that is intended to sit behind or under a patient's ear. Tubing 128a, 128b includes a second inner diameter that is greater than the first inner diameter from flared or stepped-up segments 129a, 129b to second or proximal ends 131a, 131b.

Figure 19:
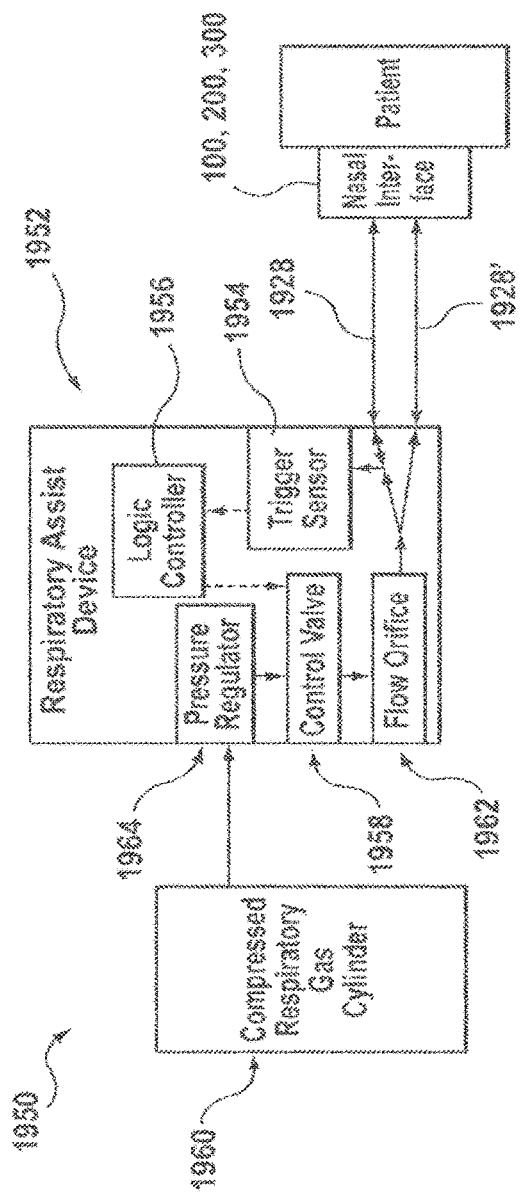
FIGS. 19 and 20 are schematic depictions of ambulatory assist ventilation (AAV) systems in accordance with embodiments hereof.
Figure 20:
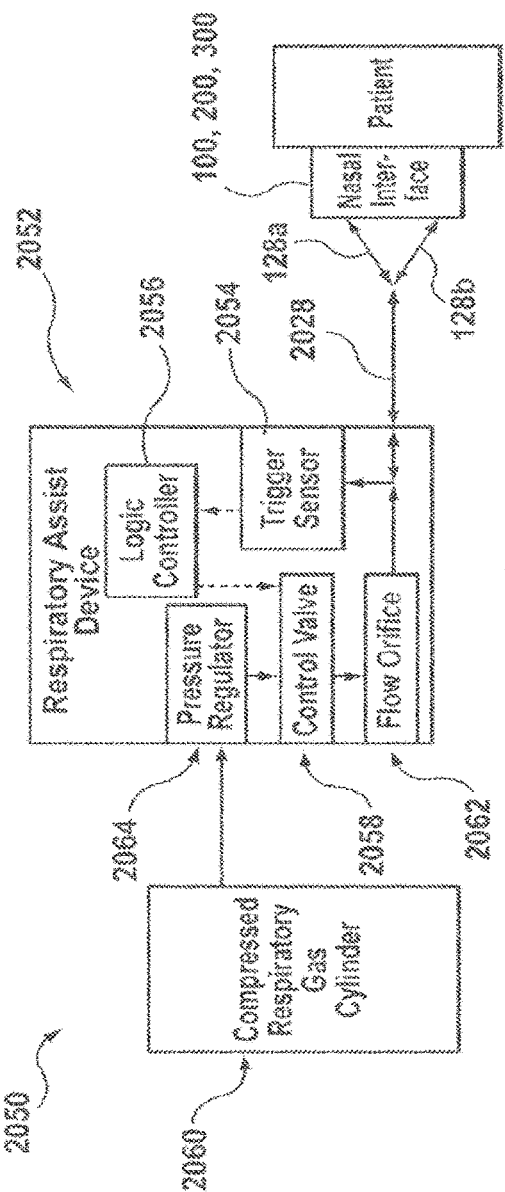

In embodiments hereof, a first inner diameter of tubing 128a, 128b may be in the range of 0.020 inch to 0.070 inch and a second inner diameter of tubing 128a, 128b may be in the range of 0.080 inch to 0.125 inch. Advantageously, the smaller first inner diameter tubing increases in diameter at flared or stepped-up segments 129a, 129b behind the patient's ear and thereby minimizes pressure drop compared to having the smaller first inner diameter tubing extend to the respiratory assist device or a Y- or T-connector. Second ends 131a, 131b of tubing 128a, 128b may each directly connect to the respiratory assist device, as depicted in the system of FIG. 19, or may connect via a T- or Y-connector to another length of tubing or hose that connects with the respiratory assist device, as depicted in the system of FIG. 20. In an embodiment, each tubing 128a, 128b may be formed from more than one segment of tubing or tubes with at least a first or proximal segment of tubing having the first inner diameter and a second or distal segment of tubing having the second inner diameter with flared or stepped-up segment 129a, 129b being a flared connector, fitting or additional segment of tubing that fluidly couples the first and second segments of tubing together while providing a gradual transition between the first and second inner diameters thereof. In another embodiment, tubing 128a, 128b may have more than one flared or stepped-up segment between the first and second ends thereof.

FIG. 10A is a simplified sectional view taken along line A-A in FIG. 10 of a patient's nostril PN with a portion of nasal interface 100 disposed therein. As depicted in FIG. 10A, a length $L_1$ of tubular body portion 125a of nasal pillow 102a is greater than a length $L_2$ of hub component 104a, with the length $L_1$ of the nasal pillow body portion being sized to fit within the nostril of a user and with a length $L_3$ being a length of hub component 104a that extends slightly proximal of the nostril opening. In embodiments hereof, a length $L_1$ of tubular body portion 125a may be in the range of 0.10 inch to 0.60 inch, a length $L_2$ of hub component 104a may be in the range of 0.05 inch to 0.40 inch and a length $L_3$ being a length of hub component 104a that extends slightly proximal of the nostril opening may be in the range of 0.050 inch to 0.30 inch. In an embodiment, a width of nasal pillow 102a at the half line, L1'/2 is equivalent to a width of the nostril opening and/or a width of hub component 104a is selected to be no wider than a rim of the nostril opening. In an embodiment, a length $L_1$ of tubular body portion 125a of nasal pillow 102a is sized to reside within the nostril of a user such that when nasal interface 100 is worn by the user connector strip 106 abuts against the columella C between the patient's nostrils while the remainder of the nasal interface 100, which includes length $L_3$ of hub component 104a, is disposed within or slightly proximal of the nostril of the user, as depicted in FIGS. 9, 10 and 10A. The use of the phrase "disposed . . . slightly proximal of the nostril of the user" is meant to convey that no part of the nasal pillow or hub component extends a distance proximal of the rim of the nostril opening that is sufficient to touch or interact with any tissue proximate or proximal of the rim of the nostril opening. In another embodiment, an overall length $L_1'$ of nasal pillow 102a is sized such that when nasal interface 100 is worn by a user the nasal pillow first end 103a does not substantially extend beyond the nostril opening of the user. In embodiments hereof, an overall length $L_1'$ of nasal pillows 102a, 102b may be in the range of 0.10 inch to 0.60 inch. The use of the phrase "does not substantially extend beyond the nostril opening of a user" is meant to convey that none of to less than a quarter of a length of the nasal pillow extends below or proximal of the rim of the nostril opening.

FIGS. 10B and 10C are sectional views taken along line A-A in FIG. 10 of a portion of nasal interface 100, with FIG. 10B depicting the delivery of respiratory gas and entrained ambient air during an inspiratory effort of the patient and FIG. 10C depicting an expiratory effort of the patient. Central hub 110a of hub component 104a is positioned at first or proximal end 103a of nasal pillow 102a so as to be substantially coaxial with distal port 101a of the nasal pillow. During an inspiratory phase of a patient wearing nasal interface apparatus 130, the flow of a pressurized respiratory gas from the plurality of delivery openings 112a of central hub 110a (represented by arrows made with dot-dashed lines in FIG. 10B) in conjunction with entrained ambient air pulled-in from ambient air apertures 116a (represented by arrows made with solid lines in FIG. 10B) produces an outflow stream that substantially fills proximal port 101a prior to exiting nasal pillow 102a and entering a respective nare of the patient. During an expiratory phase of a patient wearing nasal interface apparatus 130, the flow of the pressurized respiratory gas and thus entrainment of ambient air ceases and the patient is permitted to freely exhale through nasal interface 100 with the expired gas from the patient exiting through ambient air apertures 116a, as represented by arrows made with dashed lines in FIG. 10C. In an embodiment hereof, the size of ambient air apertures 116a, 116b and their position within nasal interface 100 to be substantially aligned with rims of the patient's nostril provides less resistance to the patient's inhalation and exhalation and particularly minimizes exhalation resistance, such that the nasal interface does not interfere with the patient's breathing out to thereby prevent undesirable "breath stacking."

In embodiments hereof, the arrangement and number of disc outlets 119a, 119b or delivery openings 112a of central hub 110a and their location proximate to or near the ambient air apertures 116a provides 300% to 400% of ambient air entrainment, which conserves the respiratory gas supply while providing a therapeutic volume of the entrained ambient air and respiratory gas mixture to the patient. In other embodiments, the arrangement and number of disc outlets 119a, 119b or delivery openings 112a of central hub 110a and their location within the nasal interface proximate to or near the ambient air apertures 116a provides a therapeutic volume of an entrained ambient air and respiratory gas mixture to the patient that has 3 to 5 times more entrained ambient air than respiratory gas, which also serves to conserve the respiratory gas supply. The afore-mentioned improvement in entrainment is realized due to the arrangement of disc outlets or delivery openings, the number of pressurized respiratory gas disc outlets or delivery openings, the minimal diameters of each disc outlet or delivery opening and the spacing, nearness and/or proximity of the disc outlet or delivery openings to the ambient air aperture(s). The arrangement of delivery openings is preferably configured in a pattern that will maximize the amount of respiratory gas flow from each of the delivery openings that is exposed to entrained ambient air while also maximizing a size of the ambient air aperture so as to permit a maximum amount of entrained ambient air to flow through and into the nasal pillows of the nasal interface. Furthermore, it is preferable to maximize the number of delivery openings, while maintaining a constant net sum of the cross-sectional areas of the openings, i.e., minimal diameters, which further increases the perimetrical amount of respiratory gas flow from each of the delivery openings that is exposed to the entrained ambient air while minimizing an internal area of the respiratory gas flow that is not exposed to the entrained ambient air. Additionally, it is preferred to locate the delivery openings in close proximity to the ambient air aperture(s) to maximize exposure of the respiratory gas flow from each delivery opening with the entrained ambient air.

The number of pressurized respiratory gas disc outlets or delivery openings, the minimal diameters of each disc outlet or delivery opening and the spacing, nearness and/or proximity of the disc outlets or delivery openings to the ambient air aperture(s) also permits the delivery of the pressurized respiratory gas relatively close to or near the entrance to the nare opening without creating discomfort to the patient due to flow impingement, and it is consideration of these factors that has led to the development of the small, lightweight and discrete nasal interfaces of embodiments hereof. The amount of fluid power exiting each discrete disc outlet or delivery opening is proportional to the mass flow rate and the square of the velocity. By design to increase entrainment and patient pressure, the fluid velocity out of each outlet or opening is sonic. Sonic flow is a physical limitation of the fluid speed exiting an outlet or opening. By minimizing the diameter of each disc outlet/delivery opening and increasing the number of disc outlets/delivery openings, the mass flow rate exiting each disc outlet/delivery opening is reduced by the total amount of outlets/openings, assuming a constant net sum of the cross-sectional areas of the openings. Therefore, for e.g., when ten outlets are to be employed as opposed to one outlet, the fluid power out of each opening would be $\frac{1}{10}$ that of a single outlet. This will reduce the discomfort transmitted to the patient due to flow impingement. With reference to FIGS. 7, 10B and 10C and as previously described above, distal surfaces 121a, 121b of central hubs 110a, 110b of hub components 104a, 104b include the plurality of delivery openings 112a, 112b formed therein with outlet discs 122a, 122b secured therein. In accordance with various nasal interface embodiments hereof, in order to affect entrainment and to assure comfortable flow to the patient, distal surfaces 121a, 121b of each central hub 110a, 110b may be one of aligned with, proximal to and distal of a proximal surface 123 of nasal pillow component 102.

Figure 11:
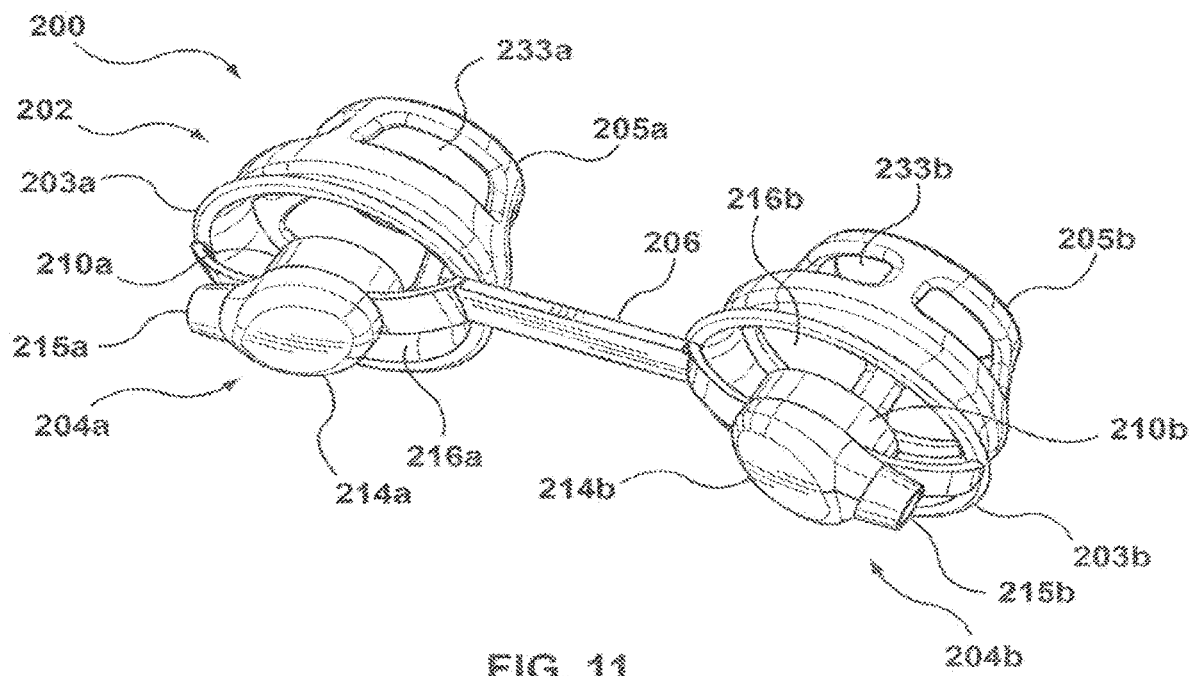
FIG. 11 is a perspective bottom view of a nasal interface device in accordance with another embodiment hereof.
Figure 12:
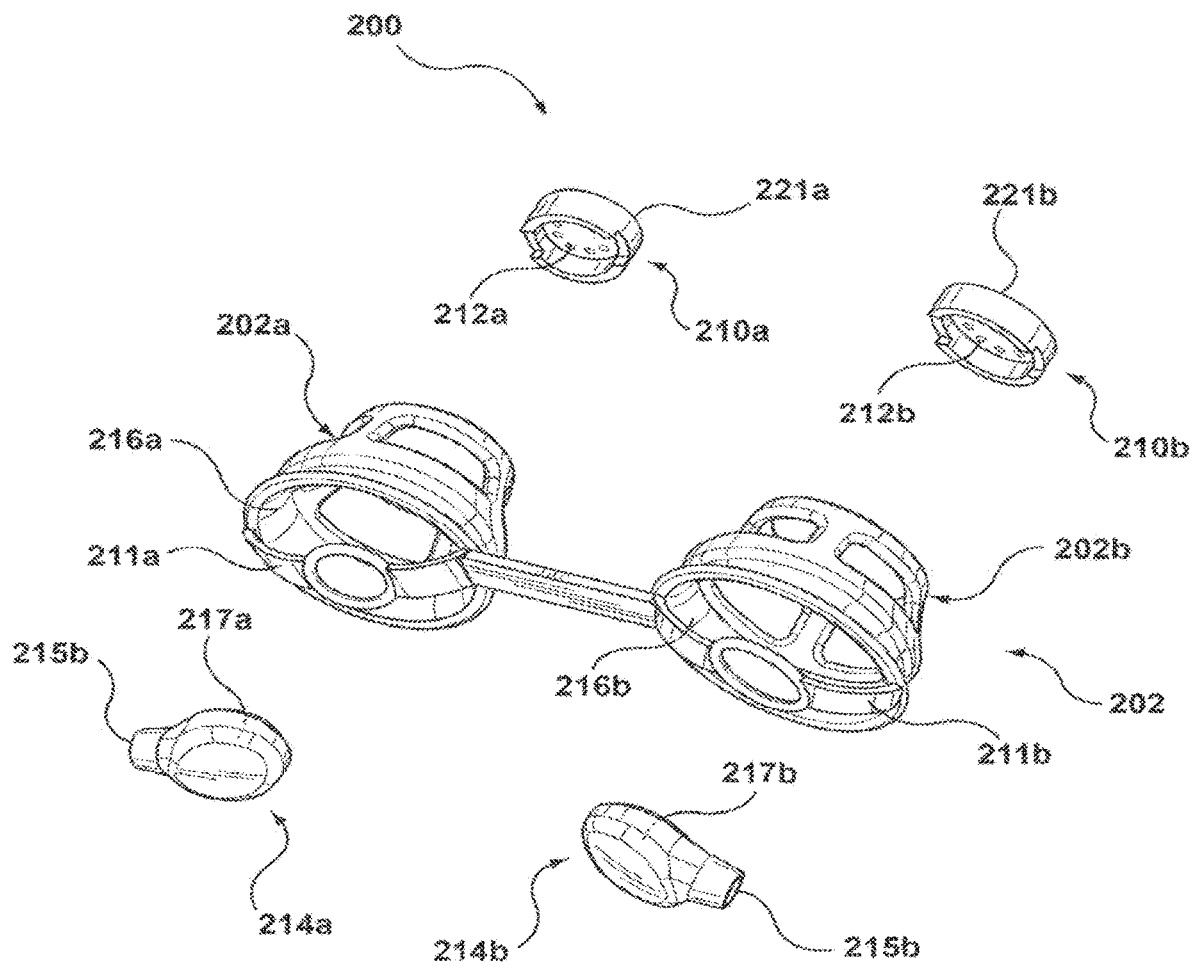
FIG. 12 is an exploded perspective view of the nasal interface device of FIG. 11 showing various subcomponents thereof.

FIG. 11 is a perspective bottom view of a nasal interface device 200 in accordance with another embodiment hereof, with FIG. 12 being an exploded perspective view of nasal interface device 200 showing various subcomponents thereof. The embodiment of FIGS. 11-15 may be used with all features described with reference to other embodiments hereof and only features and functions that differ from those already described will be detailed herein. Nasal interface 200 includes a nasal pillow component 202 and a pair of hub components 204a, 204b. Nasal pillow component 202 includes nasal pillows 202a, 202b with tubular body portions 225a, 225b having lattice-like walls that include a series of circumferentially extending apertures 233a, 233b therethrough. The lattice-like structure of nasal pillows 202a, 202b aids in anchoring the nasal pillow within a respective nare of the nasal interface wearer, while improving comfort of the wearer. Nasal pillows 202a, 202b have proximal or first ends 203a, 203b and distal or second ends 205a, 205b. A central passageway 226a, 226b is defined by tubular body portions 225a, 225b of each nasal pillow 202a, 202b from substantially a first end 203a, 203b to a respective second end 205a, 205b thereof. Nasal pillow component 202 also includes distal support structures 208a, 208b for attaching nasal pillow component 202 to hub components 204a, 204b, as described below. A connector strip 206 is a thin flexible segment of nasal pillow component 202 that extends between struts 211a, 211b proximal of first ends 203a, 203b of nasal pillows 202a, 202b, respectively, to provide flexibility and articulation between nasal pillows 202a, 202b so as to permit adjustment to the particular anatomy of a user.

Figure 13:
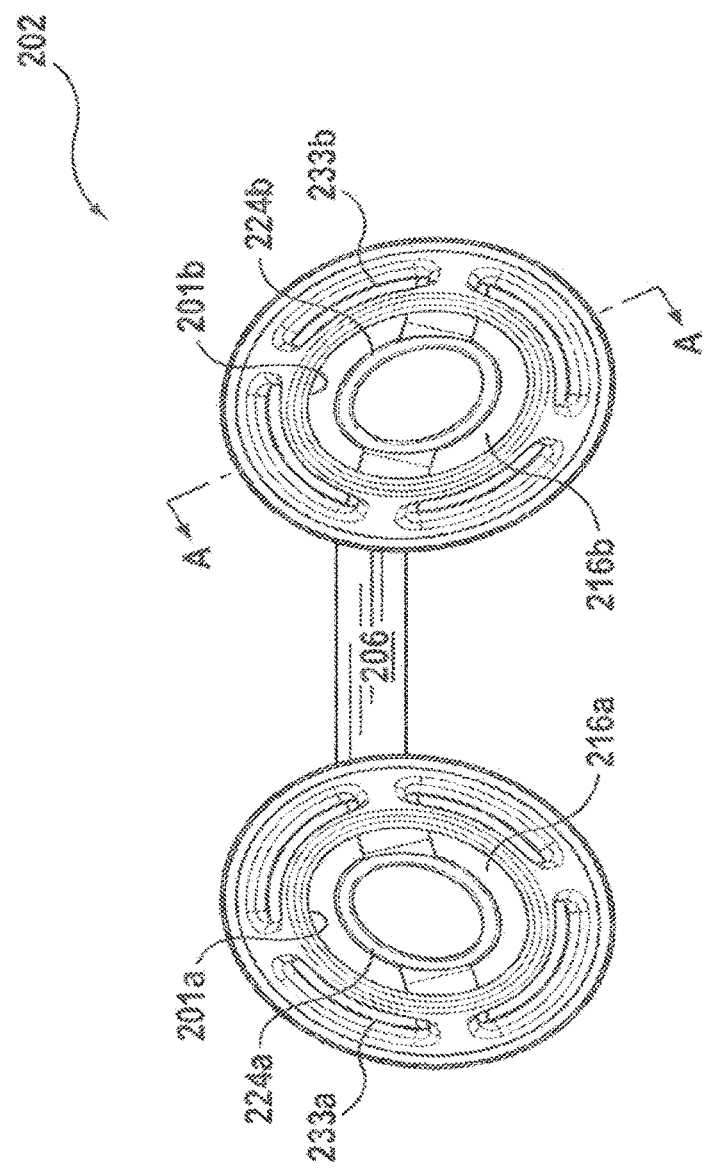
FIG. 13 is a top view of a portion of the nasal interface device of FIG. 11.
Figure 14:
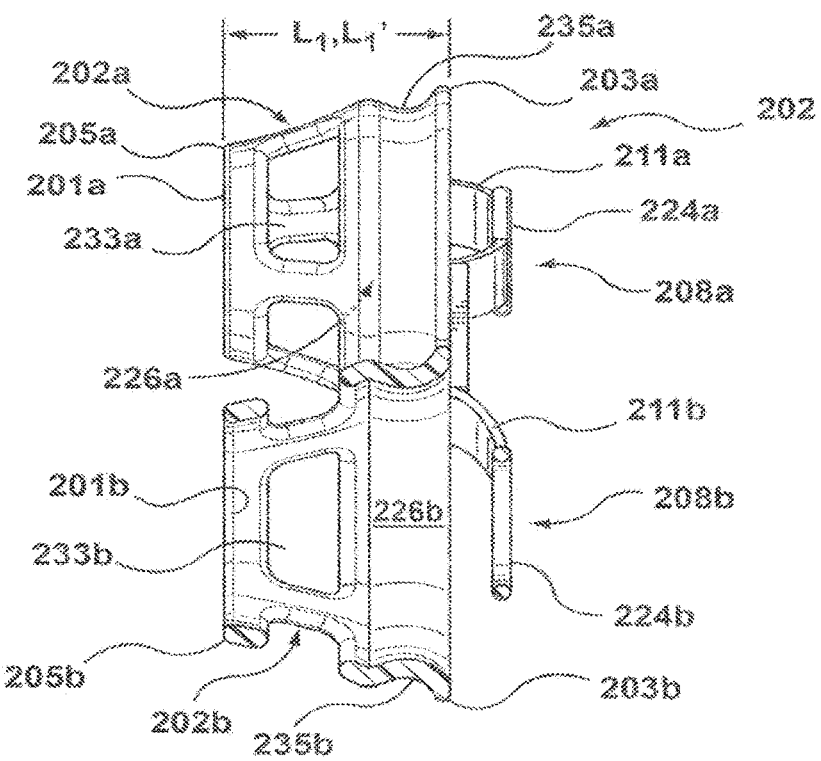
FIG. 14 is a partial sectional view of the portion of the nasal interface shown in FIG. 13 taken along line A-A thereof.
Figure 15:
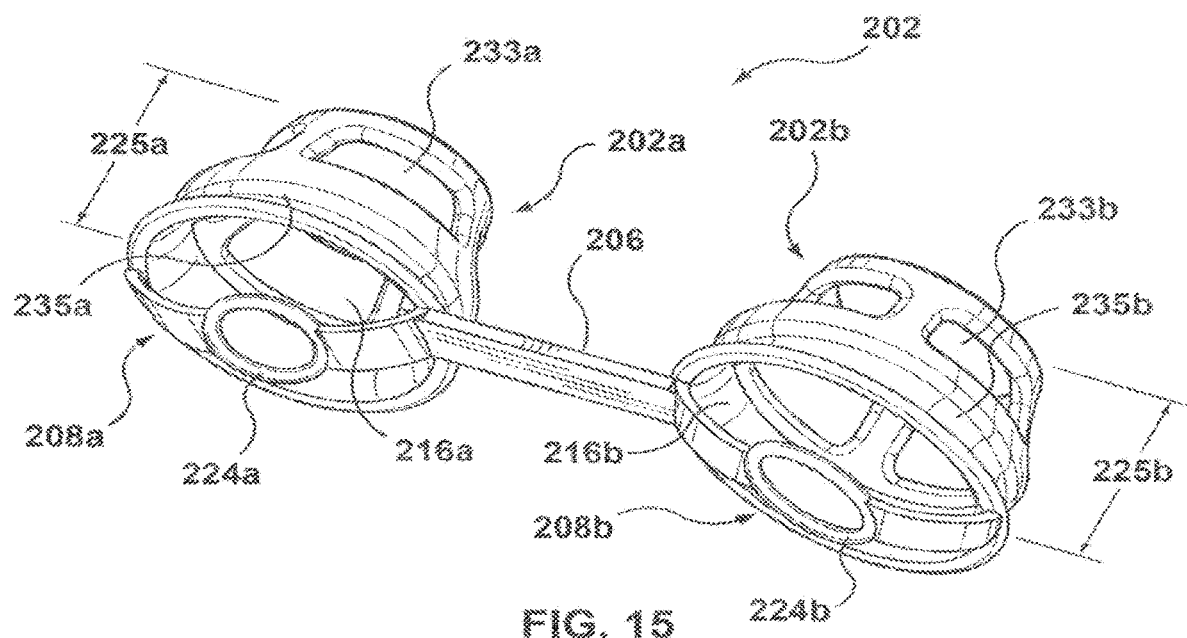
FIG. 15 is a perspective bottom view of the portion of the nasal interface shown in FIG. 13.

With reference to FIGS. 13 through 15, nasal pillow component 202 with nasal pillows 202a, 202b, connector strip 206 and distal support structures 208a, 208b is a unitary, contiguous molded component. In an embodiment, nasal pillow component 202 is of an elastomeric material, such as 30 Shore A silicone. Nasal pillows 202a, 202b are formed to have concave outer surfaces distal of first ends 203a, 203b that form grooves 235a, 235b for accommodating and/or contouring to a respective rim or lip of the nostril opening. As best shown in FIG. 15, distal support structures 208a, 208b include sealing rings 224a, 224b and struts or members 211a, 211b with each strut 211a, 211b laterally or radially extending between a respective sealing ring 224a, 224b and a respective first end 203a, 203b of a respective nasal pillow 202a, 202b. Although shown with two struts 211a, 211b, more or fewer struts may be used in support structures 208a, 208b in accordance with various embodiments hereof. Struts 211a, 211b are configured to permit a change in an aspect ratio of a cross-section of respective nasal pillows 202a, 202b from which they extend, which permits the respective nasal pillow to be squeezed radially inward or otherwise elastically deformed for insertion within a nostril and when released substantially return to their original shape to thereby anchor within a respective nostril to secure nasal interface 200 to the patient. In this manner, nasal interface 200 provides for a more comfortable and secure fit for the user. In an embodiment in which nasal pillow 202a, 202b have an oval cross-section the aspect ratio of the cross-section is the ratio of the larger diameter of the major axis of the ellipse to the smaller diameter of the minor axis of the ellipse. In an embodiment hereof, the flexibility of struts 211a, 211b permits the change in the aspect ratio of the cross-section of the respective nasal pillow 202a, 202b. In another embodiment, a shape of struts 211a, 211b permits the change in the aspect ratio of the cross-section of the respective nasal pillow 202a, 202b, such as the curved, thin and narrow strip-like or plank-like shape of struts 211a, 211b. In another embodiment, strut 211a, 211b may have a shape of a curved beam with a circular or square cross-section that permits the change in the aspect ratio of the cross-section of the respective nasal pillow 202a, 202b.

Hub components 204a, 204b include central hubs 210a, 210b having distal surfaces 221a, 221b through which a plurality of delivery openings 212a, 212b are formed and a proximal plenum structure 214a, 214b that defines an inlet 215a, 215b for receiving a compressed or pressurized respiratory gas and a plenum 217a, 217b for distributing the respiratory gas through the plurality of delivery openings 212a, 212b. Hub components 204a, 204b are attached to nasal pillow component 202 so as to be concentrically or axially disposed with respective distal ports 201a, 201b of nasal pillows 202a, 202b such that the plurality of delivery openings 212a, 212b of each central hub 210a, 210b are sized and positioned to deliver a respiratory gas within its respective nasal pillow. In an embodiment, distal surfaces 221a, 221b of central hubs 210a, 210b have a thickness or depth of less than 0.040 inch with each delivery opening 212a, 212b having a diameter of less than 0.010 inch.

In an embodiment, each of the plurality of delivery openings 212a, 212b forms a pattern in the distal surface of its respective central hub that corresponds to a shape of the corresponding distal port 201a, 201b. In an embodiment, hub components 204a, 204b are attached to nasal pillow component 202 by positioning a respective sealing ring 224a, 224b between its corresponding central hub 210a, 210b and proximal plenum structure 214a, 214b, and securing the respective central hub 210a, 210b and proximal plenum structure 214a, 214b together with the respective sealing ring 224a, 224b sandwiched therebetween. In embodiments hereof, each proximal plenum structure 214a, 214b is attached to its respective central hub 210a, 210b by any suitable means known to one of skill in the art, such as by a snap fit, gluing or welding.

In an embodiment hereof, outlet discs similar to outlet discs 122a, 122b may be used with central hubs 210a, 210b with the disc outlets being sized and configured to produce/deliver the pressurized respiratory gas/entrained air outflow stream to the respective nasal pillow proximal ports 201a, 201b. In such an embodiment, each of the plurality of delivery openings 212a, 212b would be adapted to have a diameter that is slightly greater than the diameter of a corresponding disc outlet such that each delivery opening 212a, 212b is large enough to not impede on the flow exiting from a corresponding disc outlet or outlets.

A series of ambient air apertures 216a, 216b are formed between respective portions of annular first ends 203a, 203b of nasal pillows 202a, 202b, adjacent struts 211a, 211b and central hubs 210a, 210b such that as shown in FIGS. 11, and 13-15, the series of ambient air apertures 216a, 216b of nasal interface 200 are disposed proximate to or near first ends 203a, 203b of each nasal pillow 202a, 202b, respectively, to substantially surround the respective hub components 204a, 204b disposed therein.

Nasal interface device 200 is fluidly connectable to a respiratory assist device via tubing for receiving the respiratory gas therefrom, as described above with reference to FIG. 8 that depicts nasal interface apparatus 130. Nasal interface device 200 also functions in a similar manner as described above with reference to the previous embodiment. More particularly with reference to FIG. 11A, which is a sectional view of a portion of nasal interface apparatus 200 within a patient's nostril, during an inspiratory phase of a patient wearing nasal interface device 200 as part of apparatus 130, the flow of a pressurized respiratory gas from the plurality of delivery openings 212*b* of central hub 210*b* in conjunction with entrained ambient air drawn from ambient air apertures 216*b* produces an outflow stream that substantially fills proximal port 201*b* prior to exiting nasal pillow 202*b* and entering a respective nare of the patient. During an expiratory phase of a patient wearing nasal interface device 200 as part of apparatus 130, the flow of the pressurized respiratory gas and thus entrainment of ambient air ceases and the patient is permitted to freely exhale through nasal interface 200 with the expired gas from the patient exiting through ambient air aperture 216*b*.

Figure 11A:
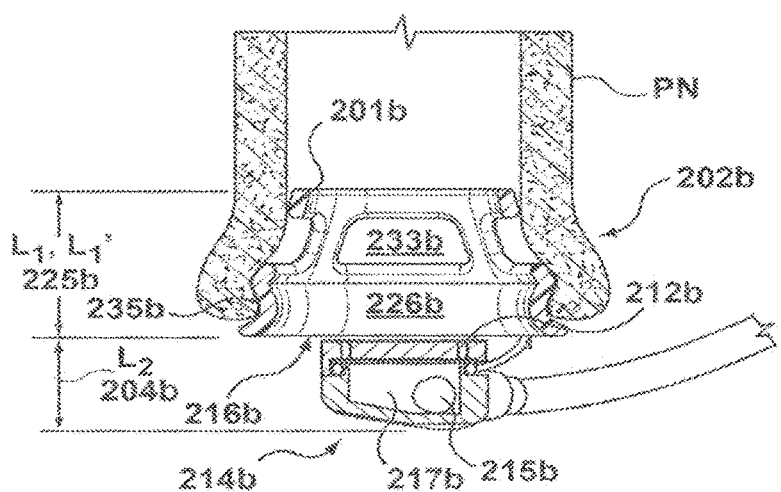
FIG. 11A is a sectional view of a portion of the nasal interface apparatus shown in FIG. 11 within a patient's nostril.

In an embodiment, an overall length $L_1'$ of each nasal pillow 202*a*, 202*b* is the same as a length $L_1$ of its tubular body portion 225*a*, 225*b* and is sized such that when nasal interface 200 is worn by a user the nasal pillow first end 203*a*, 203*b* does not extend beyond the nostril opening of the user with a rim or lip of the nostril opening fitting or abutting against a respective groove 235*a*, 235*b* of the nasal pillow 202*a*, 202*b*. With reference to FIG. 11A, length $L_1$, $L_1'$ of tubular body portion 225*b*/nasal pillow 202*b* is greater than a length $L_2$ of hub component 204*b*, with length $L_1$, $L_1'$ of tubular body portion 225*b*/nasal pillow 202*b* being sized to fit within the nostril of a user. In embodiments hereof, a length $L_1$ of tubular body portions 225*a*, 225*b* may be in the range of 0.10 inch to 0.60 inch and a length $L_2$ of hub components 204*a*, 204*b* may be in the range of 0.05 inch to 0.40 inch.

Figure 16:
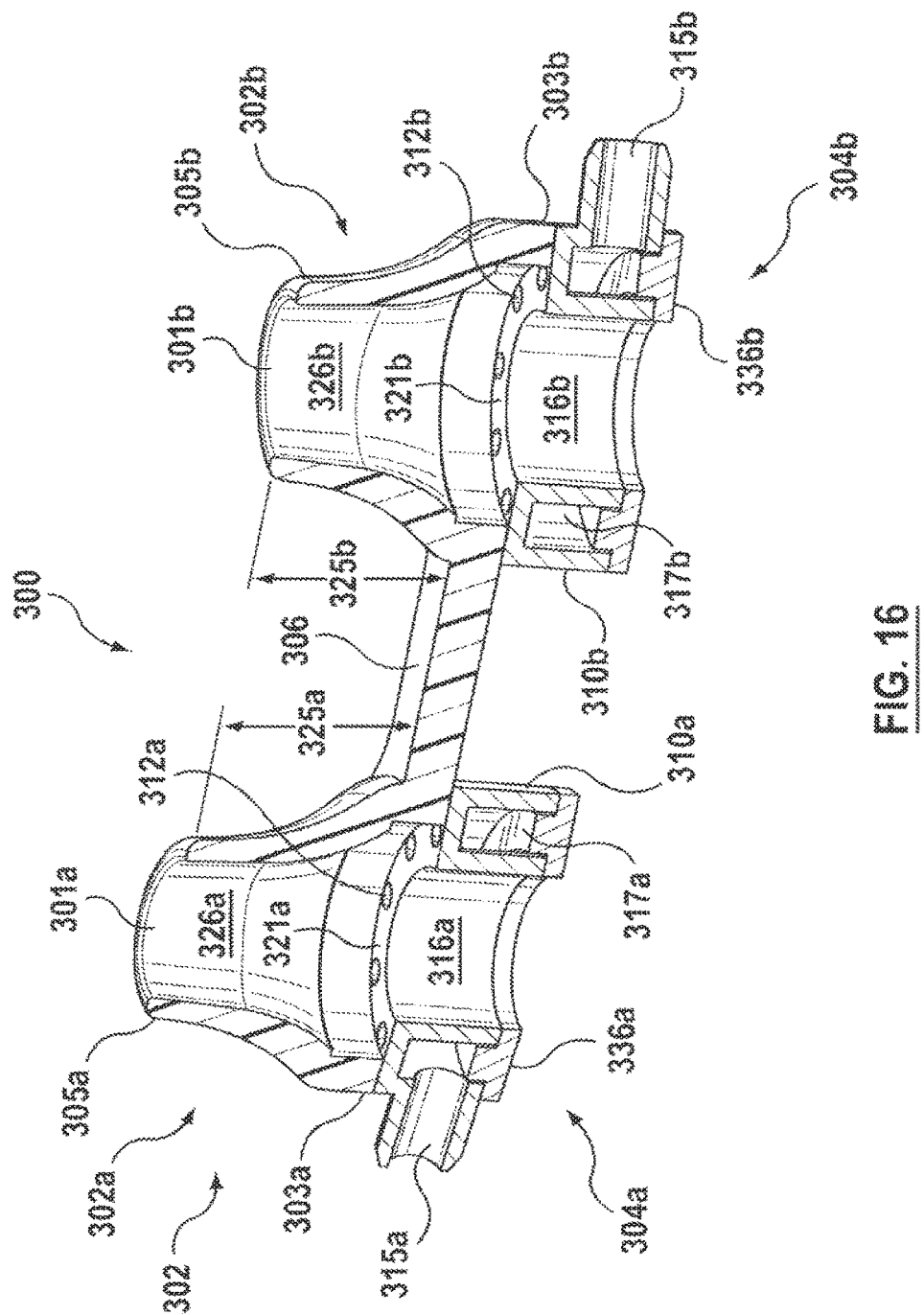
FIG. 16 is a sectional view of a nasal interface device in accordance with another embodiment hereof.

FIG. 16 is a sectional view of a nasal interface device 300 in accordance with another embodiment hereof, with FIGS. 17 and 18 being exploded perspective views showing various subcomponents of nasal interface device 300. The embodiment of FIGS. 16-18 may be used with all features described with reference to other embodiments hereof and only features and functions that differ from those already described will be detailed herein. Nasal interface 300 includes a nasal pillow component 302 and a pair of annular hub components 304*a*, 304*b*. "Annular" as used to describe various features of embodiments hereof means substantially shaped like a ring, hollow cylinder, or toroid and is not meant to be limited to a such shapes having a circular perimeter but is intended to include various other perimetrical shapes such as oval, elliptical, etc. Nasal pillow component 302 includes nasal pillows 302*a*, 302*b* with tubular body portions 325*a*, 325*b* defining central passageways 326*a*, 326*b* from substantially first or proximal ends 303*a*, 303*b* to respective second ends 305*a*, 305*b* thereof. Nasal pillow component 302 also includes a connector strip 306 that extends between nasal pillow first ends 303*a*, 303*b* to provide flexibility and articulation between nasal pillows 302*a*, 302*b* so as to permit adjustment to the particular anatomy of a user. In an embodiment, nasal pillow component 302 with nasal pillows 302*a*, 302*b* and connector strip 306 is a molded component of an elastomeric material, such as 30 Shore A silicone.

Annular hub components 304*a*, 304*b* are concentrically disposed with or at first ends 303*a*, 303*b* of nasal pillows 302*a*, 302*b*, respectively. With reference to the exploded views of nasal interface 300 depicted in FIGS. 17 and 18, each annular hub component 304*a*, 304*b* includes an annular hub 310*a*, 310*b* with a plurality of delivery openings 312*a*, 312*b* formed through distal surfaces 321*a*, 321*b* thereof, and a proximal annular cap 336*a*, 336*b*. The plurality of delivery openings 312*a*, 312*b* are periodically spaced about distal surfaces 321*a*, 321*b* so as to circumferentially surround centrally located ambient air apertures 316*a*, 316*b*. In conjunction with the positioning of the plurality of delivery openings 312*a*, 312*b* near to the ambient air apertures 316*a*, 316*b*, the plurality of delivery openings 312*a*, 312*b* are sized to produce/deliver the pressurized respiratory gas/entrained air outflow stream to the respective nasal pillow proximal ports 301*a*, 301*b*. In an embodiment, each of the plurality of delivery openings 312*a*, 312*b* has a circular cross-section. Annular hubs 310*a*, 310*b* define respective inlets 315*a*, 315*b* for receiving a respiratory gas from a respiratory assist device (not shown), and in conjunction with respective annular caps 336*a*, 336*b* form an enclosed space or plenum 317*a*, 317*b* for distributing the respiratory gas to the plurality of delivery openings 312*a*, 312*b* of the annular hub component. Annular caps 336*a*, 336*b* include distally extending annular flanges 318*a*, 318*b* that snap, or are otherwise secured by gluing or welding, within corresponding recesses within annular hubs 310*a*, 310*b*.

Annular hubs 310*a*, 310*b* of annular hub components 304*a*, 304*b* are positioned to be coaxial with respective distal ports 301*a*, 301*b* of nasal pillows 302*a*, 302*b* such that the plurality of delivery openings 312*a*, 312*b* of each annular hub component are positioned to deliver a respiratory gas within its respective nasal pillow. A central ambient air aperture 316*a*, 316*b* is formed by respective inner circumferential surfaces of annular hub components 304*a*, 304*b* so as to be disposed proximate to or near the plurality of delivery openings 312*a*, 312*b* of the respective annular hubs 310*a*, 310*b* at first ends 303*a*, 303*b* of nasal pillows 302*a*, 302*b*, respectively, as shown in FIG. 16.

In an embodiment hereof, outlet discs similar to outlet discs 122*a*, 122*b* may be used with central hubs 310*a*, 310*b* with the disc outlets being sized and configured to produce/deliver the pressurized respiratory gas/entrained air outflow stream to the respective nasal pillow proximal ports 301*a*, 301*b*. In such an embodiment, each of the plurality of delivery openings 312*a*, 312*b* would be adapted to have a diameter that is slightly greater than the diameter of a corresponding disc outlet such that each delivery opening 312*a*, 312*b* is large enough to not impede on the flow exiting from a corresponding disc outlet or outlets.

Nasal interface device 300 is fluidly connectable to a respiratory assist device via tubing for receiving the respiratory gas therefrom, as described above with reference to FIG. 8 that depicts nasal interface apparatus 130. Nasal interface device 300 also functions in a similar manner as described above with reference to nasal interface device 100. More particularly, during an inspiratory phase of a patient wearing nasal interface device 300 as part of apparatus 130, the flow of a pressurized respiratory gas from the plurality of delivery openings 312*a*, 312*b* of annular hubs 310*a*, 310*b* in conjunction with entrained ambient air drawn from centrally located ambient air apertures 316*a*, 316*b* produces an outflow stream that substantially fills proximal ports 301*a*, 301*b* prior to exiting nasal pillows 302*a*, 302*b* and entering a respective nare of the patient. During an expiratory phase of a patient wearing nasal interface device 300 as part of apparatus 130, the flow of the pressurized respiratory gas and thus entrainment of ambient air ceases and the patient is permitted to freely exhale through nasal interface 300 with the expired gas from the patient exiting through centrally located ambient air apertures 316*a*, 316*b*.

Figure 16A:
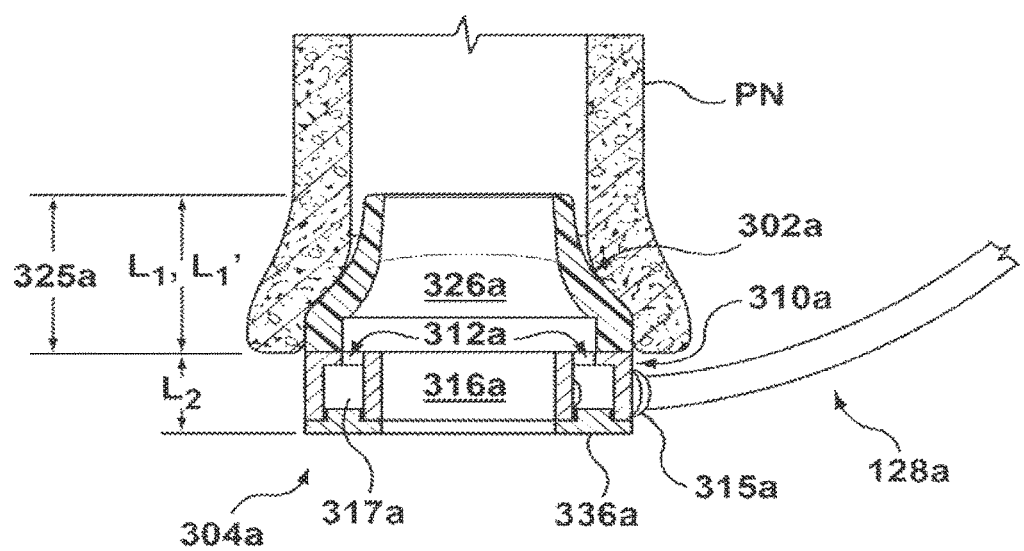
FIG. 16A is a sectional view of a portion of the nasal interface apparatus of FIG. 16 positioned within a patient's nostril.

FIG. 16A is a sectional view of a portion of nasal interface apparatus 300 of FIG. 16 positioned within a patient's nostril. An overall length $L1'$ of each nasal pillow 302*a*, 302*b* is the same as a length $L1$ of its tubular body portion 325*a*, 325*b* and is sized such that when nasal interface 300 is worn by a user the nasal pillow first end 303*a*, 303*b* does not extend beyond the nostril of the user with a rim or lip of the nostril opening abutting against a respective first end 303a, 303b of the nasal pillow 302a, 302b. As depicted in FIG. 16A, length $L_1$, $L_1'$ of tubular body portion 325a/nasal pillow 302a is greater than a length $L_2$ of annular hub component 304a, with length $L_1$, $L_1'$ of tubular body portion 325a/nasal pillow 302a being sized to fit within the nostril of a user. In embodiments hereof, a length $L_1$ of tubular body portions 325a, 325b may be in the range of 0.10 inch to 0.60 inch and a length $L_2$ of hub components 304a, 304b may be in the range of 0.05 inch to 0.40 inch. In an embodiment, a length $L_1$ of tubular body portion 325a of nasal pillow 302a is sized to reside within the nostril of a user such that when nasal interface 300 is worn by the user connector strip 306 abuts against the columella C between the patient's nostrils while the remainder of the nasal interface 300, which includes annular hub component 304a, is disposed within or slightly proximal of the nostril of the user, as depicted in FIG. 16A. The use of the phrase "disposed . . . slightly proximal of the nostril of the user" is meant to convey that no part of the nasal pillow or hub component extends a distance proximal of the rim of the nostril opening that is sufficient to touch or interact with any tissue proximate or proximal of the rim of the nostril opening.

FIGS. 19 and 20 are schematic depictions of ambulatory assist ventilation (AAV) systems 1950, 2050 in accordance with embodiments hereof that may include any one of nasal interface devices 100, 200, 300, 400, 500, 600 as described above and a respiratory assist device 1952, 2052. In embodiments hereof, respiratory assist device 1952, 2052 are designed to be small and lightweight compared to existing respiratory ventilators which permits the device to be ambulatory. Respiratory assist device 1952, 2052 can either be worn by the user using a belt clip, shoulder strap or while residing in a pack such as a backpack or waist pack. Respiratory assist device 1952, 2052 can also be attached to the user's oxygen source, eliminating the burden to the user of carrying the device. Common functionalities of AAV systems 1950, 2050 will be described together herein. AAV systems 1950, 2050 deliver mechanical ventilatory support or positive airway pressure to a patient, while permitting less encumbered movement so as to facilitate mobility of the patient and to allow activities of daily living. As a patient breathes in through one of nasal interface 100, 200, 300, 400, 500, 600, a negative pressure develops within the nasal pillows of the nasal interface that gets communicated through one or more sensing ports of the nasal interface to respiratory assist device 1952, 2052 and more particularly to a trigger or pressure sensor 1954, 2054 contained therein. With reference to the embodiment of FIG. 19, a continuous fluid flow passageway extends via tubing 1928 between trigger sensor 1954 and a central passageway of only one nasal pillow, with tubing 1928 having a first or proximal end coupled to respiratory assist device 1952 and a second or distal end couple to an inlet of the corresponding hub component of the nasal pillow. With reference to the embodiment of FIG. 20, a continuous fluid flow passageway extends via tubing 2028 between trigger sensor 2054 and central passageways of each of the pair of nasal pillows, with tubing 2028 having a first or proximal end coupled to respiratory assist device 2052 and a second or distal end coupled to a connector or fitting that couples to two tubes or length of tubing, such as tubing 128a, 128b shown in FIG. 8, that are attached to respective inlets of the hub components of the pair of nasal pillows.

Trigger sensor 1954, 2054 are configured to sense a negative pressure associated with an inspiratory phase of breathing, even a slight negative pressure, and when the negative pressure is sensed at a trigger value, logic controllers 1956, 2056 in response thereto open a control or solenoid valve 1958, 2058 to permit compressed respiratory gas to flow from compressed respiratory gas source, such as gas cylinders or reservoirs 1960, 2060, to pressure regulators 1964, 2064, which reduce the respiratory gas pressure, and then through respective flow orifice 1962, 2062 of the respiratory assist device to the nasal interface. In the embodiment of FIG. 19, the compressed respiratory gas flows to nasal interface 100, 200, 300 through tubing 1928, 1928', which in embodiments in accordance herewith may be or include lengths of tubing 128a, 128b as described above. In the embodiment of FIG. 20, the compressed respiratory gas flows to nasal interface 100, 200, 300 through tubing 2028 and 128a, 128b. The logic controllers 1956, 2056 are programmed to open control valves 1958, 2058 for a percentage of an inspiratory period and then to turn-off or close the control valve 1956, 2056/flow orifice 1962, 2062 until after exhalation. In this manner a patient or wearer of nasal interface 100, 200, 300 is able to freely exhale through the nasal interface, as described above.

In embodiments hereof, one or more of tubing 128a, 128b, 1928, 2028 defines a single lumen that is used both to provide fluid communication between the one or more sensing ports or openings of a corresponding hub component(s) of the nasal interface and the trigger sensor or pressure sensor of the respiratory assist device, and to deliver the compressed respiratory gas from the flow orifice of the respiratory assist device to the corresponding hub component(s) of the nasal interface. Single lumen tubing may be effectively used for combined sensing and respiratory gas delivery functionalities in embodiments hereof due to the efficient delivery of the compressed respiratory gas that is possible with nasal interfaces made in accordance with embodiments hereof. The efficient delivery of the compressed respiratory gas allows the use of regulated pressure respiratory gas, such as a compressed respiratory gas of less than 20 PSI, that does not adversely affect the trigger/pressure sensor during delivery of the lower pressure respiratory gas to the nasal pillows, such that the trigger/pressure sensor retains its functionality to sense very low pressures associated with triggering the next delivery of the respiratory gas. This is in contrast to NIOV systems that require provision of compressed respiratory gas at 50 PSI which is outside the operating range of available oxygen concentrator systems. The use of a single lumen tube allows the reduction of the overall diameter of the tubing as compared to dual or multiple lumen tubing. This reduction in diameter allows further reduction in the interface size and the amount of 'bulk' that is strung across the users face. Additionally, a single lumen tube reduces the complexity of the circuit assembly by simplifying bifurcation points as well as connections to the interface and the respiratory assist devices as compared to multiple lumen tubing.

In various embodiments in accordance with the AAV system of FIG. 19, a sensing opening or openings of nasal interfaces 100, 200, 300, 400, 500, 600 may be one or more of the delivery openings of one of the hub components of the nasal interface. For example, sensing openings of a nasal interface 100 used with AAV device 1950 may be either the plurality of delivery openings 112a of hub component 104a, or alternatively may be the plurality of delivery openings 112b of hub component 104b depending upon which of the hub components 102a, 102b is connected via tubing 1928 to trigger/pressure sensor 1954 of respiratory assist device 1952.

In various embodiments in accordance with the AAV system of FIG. 20, a sensing opening or openings of nasal interfaces 100, 200, 300, 400, 500, 600 may be one or more of the delivery openings of each of the hub components of the nasal interface. For example, sensing openings of a nasal interface 100 used with AAV device 2050 may be the plurality of delivery openings 112a of hub component 104a and the plurality of delivery openings 112b of hub component 104b that are connected via tubing 128a, 128b and tubing 2028 to trigger/pressure sensor 2054 of respiratory assist device 2052.

Figure 21:
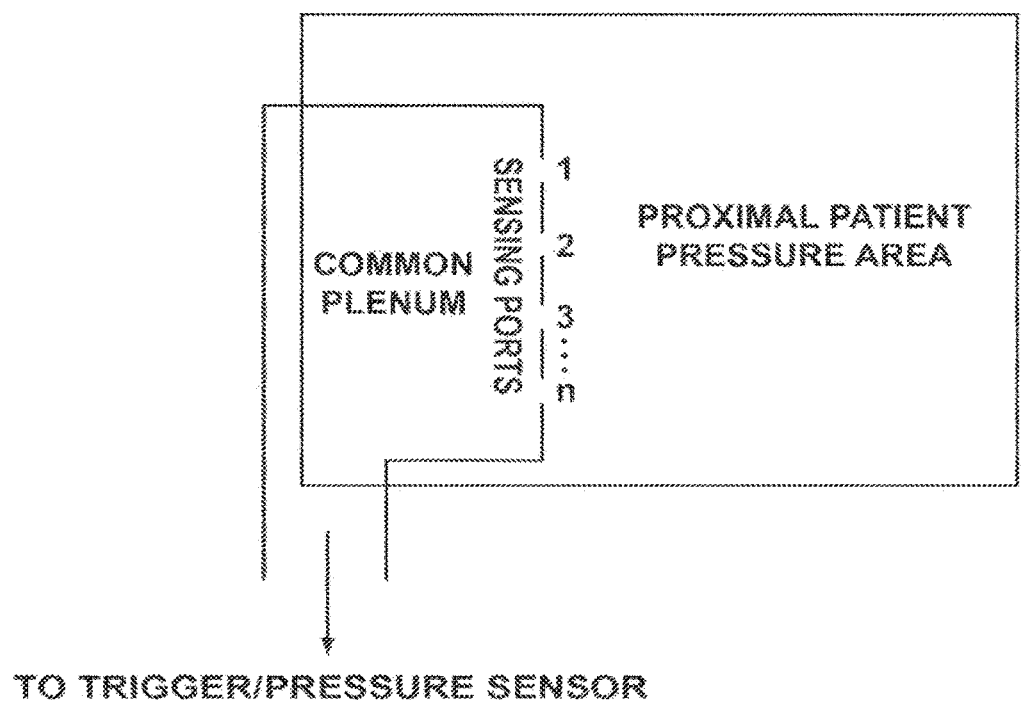
FIG. 21 is a schematic depiction of multiple pneumatically common sensing ports in accordance with embodiment hereof.

FIG. 21 is a schematic depiction of multiple pneumatically common sensing ports in accordance with embodiment hereof. AAV systems in accordance with embodiments hereof that contain multiple sensing ports or openings that have pneumatic commonality via a plenum, such as one or both plenums 117, 217, 317 of hub components 104, 204, 304 hereof, prior to communicating to a pressure sensing device, such as trigger/pressure sensors 1954, 2054, have at least two fundamental benefits. By spreading out locations of sensing ports/openings over an area, such as schematically represented by sense ports 1, 2, 3 . . . n in FIG. 21 and represented by delivery openings 112, 212, 312 in embodiments above, the pressure communicated to the trigger/pressure sensor of AAV systems 1952, 2052 will be roughly equivalent to the average of the pressure measured at each discrete sensing port across that area or $P_{sensor.aprxeq.}(P_1+P_2+P_3+ \ldots +P_n)/n$, with n being the total number of sensing ports.

With the sensing ports properly distributed over a surface of the plenum, such as when the sensing ports are the delivery openings as disclosed in accordance with embodiments hereof, a preferred average pressure across a sensing area may be established, which will reduce or eliminate the effect of localized velocity pressures that may occur at a single sensing port location. More particularly in known systems, velocity pressure at a single sensing port location, depending on flow direction, can disadvantageously either increase or reduce the static pressure measurement and thereby may yield erroneous pressure measurements that can ultimately affect the AAV system's ability to match the spontaneous breathing pattern of the user resulting in the system undesirably triggering out of synch. Such situations are avoided in accordance with embodiments hereof that include multiple sensing ports or openings that have pneumatic commonality via a plenum as described herein.

Additionally, with a size or diameter of each sensing port or opening being small relative to the plenum volume, multiple pneumatically common sensing ports in accordance with embodiments hereof will act as a low pass filter between the source pressure of the respiratory gas, a proximal patient pressure, and the trigger/pressure sensor. The low pass filter affect is created by and a function of the restriction of the orifices and the compliance of the plenum. If the restriction is increased, such as by reducing a size of the sensing opening, and/or the compliance of the plenum were to increase, such as by using a larger plenum, then the amount of filtering would increase. The low pass filtering affect is advantageous as it may improve the AAV systems synchrony with the patient by reducing false or missed triggers that may otherwise be caused by a higher frequency noise signal that occurs without the low pass filter affect.

Figure 22:
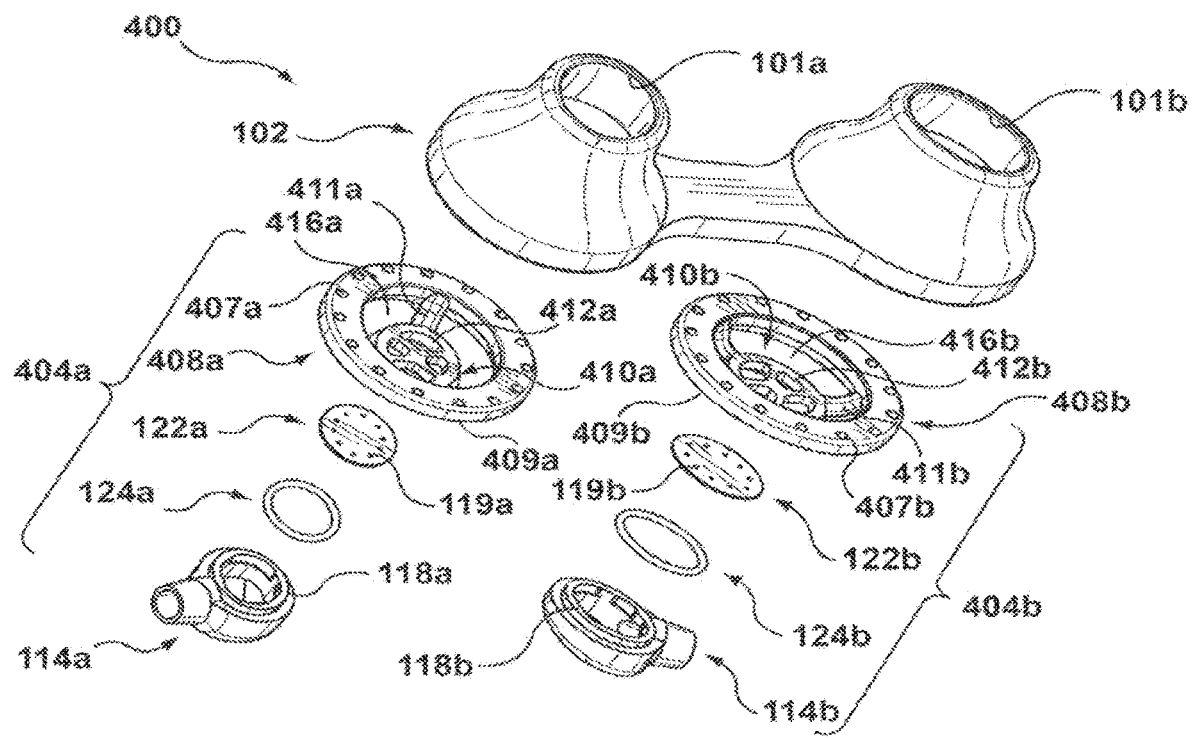
FIG. 22 is an exploded perspective view of a nasal interface device in accordance with another embodiment hereof showing various subcomponents thereof.
Figure 23:
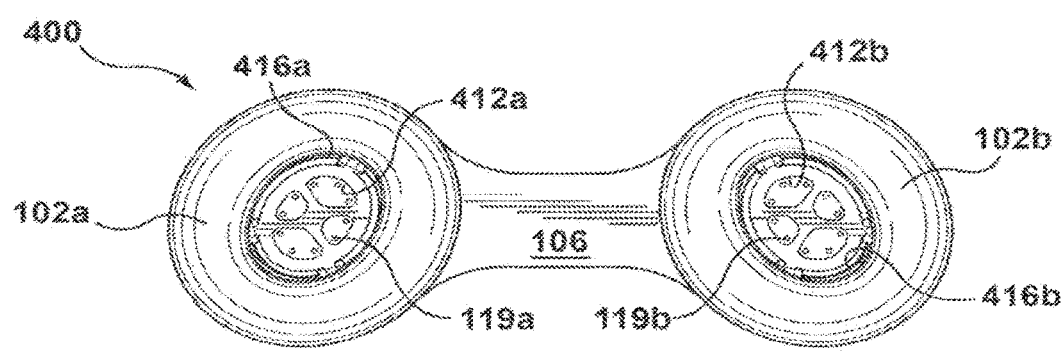
FIG. 23 is a top view of the nasal interface device of FIG. 22.

FIG. 22 is an exploded perspective view of a nasal interface device 400 in accordance with another embodiment hereof that shares features with nasal interface device 100 of FIGS. 1-7, with FIG. 23 depicting a top view of nasal interface device 400. The embodiment of FIGS. 22 and 23 may be used or adapted for use with all features described with reference to other embodiments hereof and only features and functions that differ from those already described will be detailed herein. Nasal interface 400 includes nasal pillow component 102 and a pair of hub components 404a, 404b. Each hub component 404a, 404b includes a distal support structure 408a, 408b, a central hub 410a, 410b with a plurality of delivery openings 412a, 412b, outlet discs 122a, 122b having a plurality of outlets 119a, 119b, seals 124a, 124b and proximal plenum structures 114a, 114b.

Hub components 404a, 404b, as described above, are attached to nasal pillow component 102 by respective annular rims 409a, 409b, each of which in the embodiment shown in FIGS. 22 and 23 includes a series of post-forming apertures 407a, 407b that receive a material of nasal pillow component 102 there through in an over-molding process that is used to connect the structures together. In another embodiment, nasal pillow component 102 may be glued or otherwise attached to annular rims 409a, 409b of hub components 404a, 404b. A series of ambient air apertures 416a, 416b are formed between respective annular rims 409a, 409b, adjacent spokes 411a, 411b and central hubs 410a, 410b.

The plurality of delivery openings 412a, 412b of each hub component 404a, 404b are spaced about a perimeter of distal face 421a, 421b of respective central hub 410a, 410b and are sized to be large enough to not impede on the flow exiting from two or more disc outlets 119a, 119b. Thus in the embodiment of FIGS. 22 and 23, the plurality of outlets 119a, 119b of outlet discs 122a, 122b do not directly correspond in number and arrangement to the plurality of delivery openings 412a, 412b of respective central hubs 410a, 410b. Outlet discs 122a, 122b and seals 124a, 124b are disposed within proximal recesses (not shown) of central hubs 410a, 410b such that the two or more disc outlets 119a, 119b substantially align with a corresponding central hub delivery opening 412a, 412b. In order to assure alignment of disc outlets 119a, 119b and delivery openings 412a, 412b, outlet discs 122a, 122b are held or pressed against respective proximal faces (not shown) of central hubs 410a, 410b by respective annular flanges 118a, 118b of proximal plenum structures 114a, 114b with seals 124a, 124b therebetween.

Figure 24:
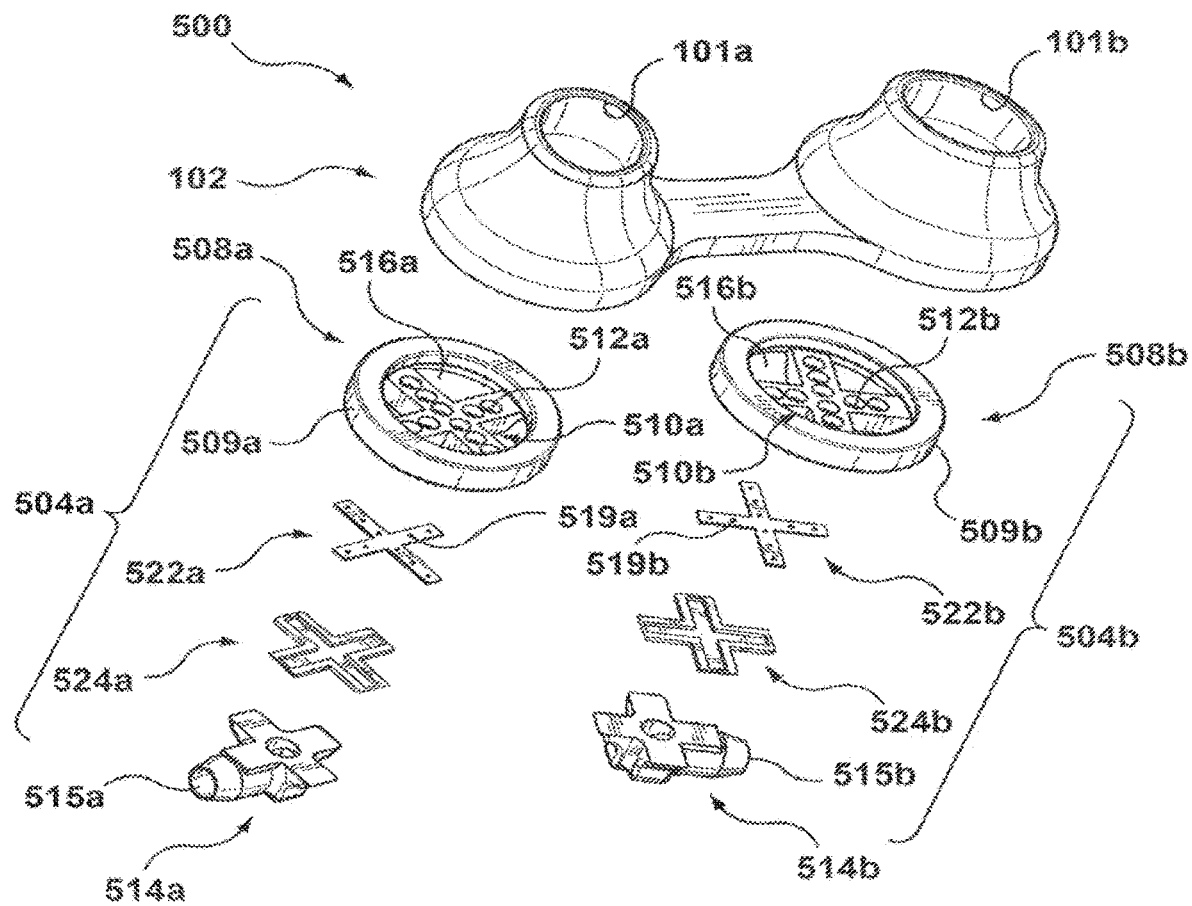
FIGS. 24 and 25 are exploded perspective views of a nasal interface device in accordance with another embodiment hereof showing various subcomponents thereof.
Figure 26:
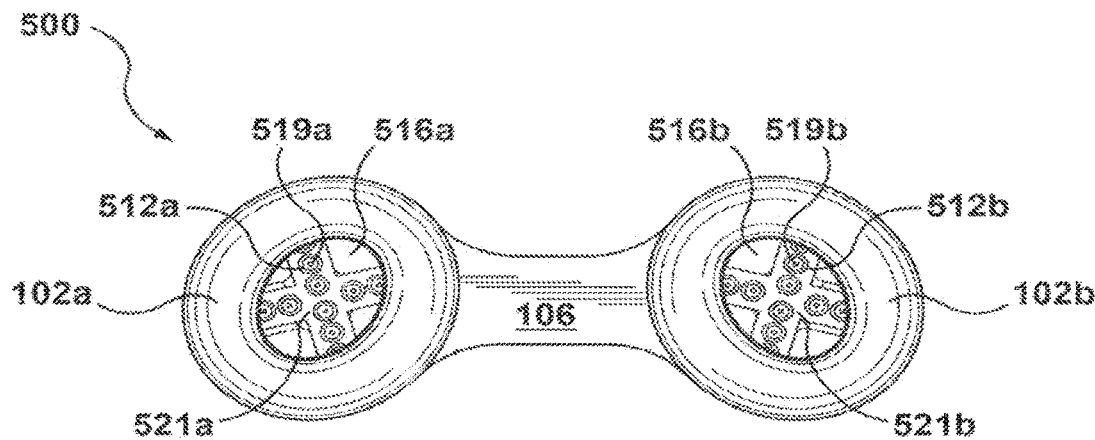
FIG. 26 is a top view of the nasal interface device of FIGS. 24 and 25.
Figure 25:
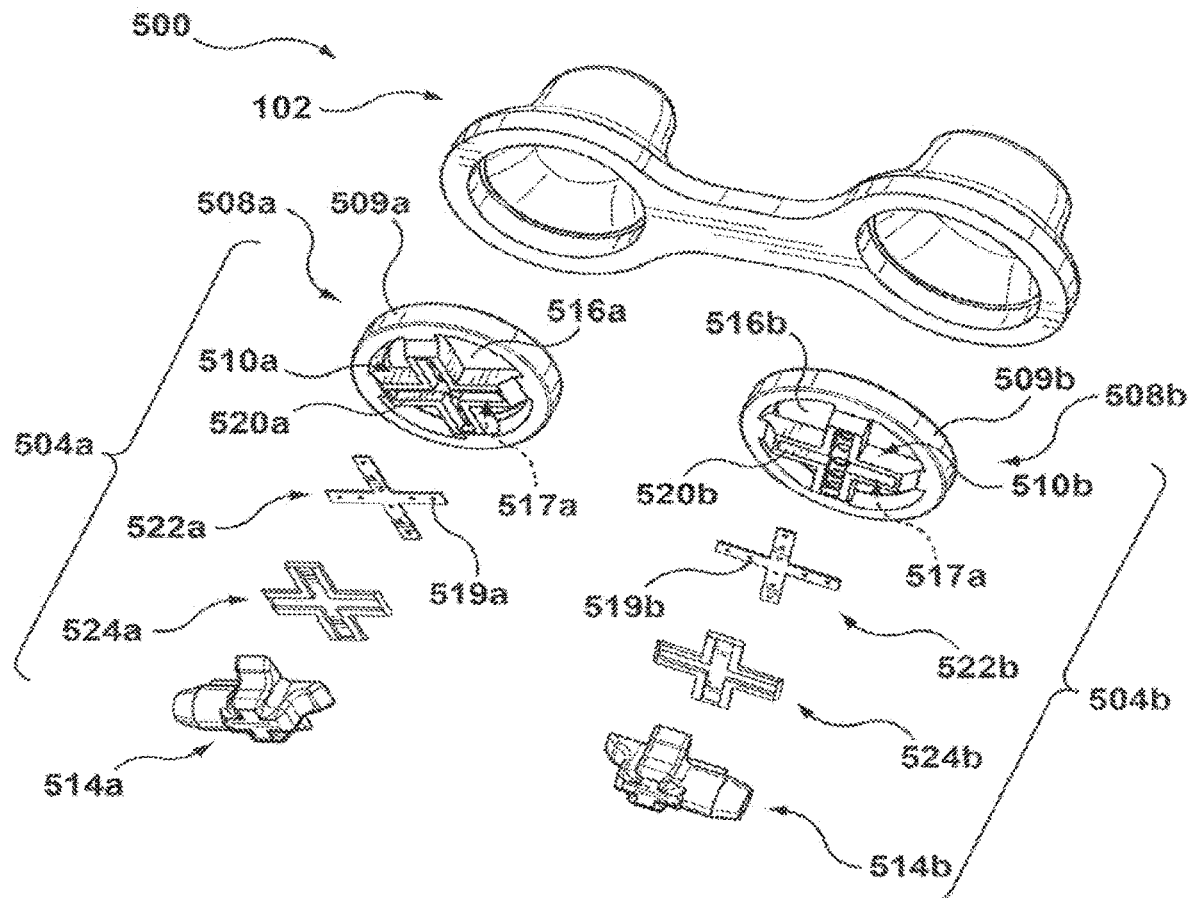
Figure 27:
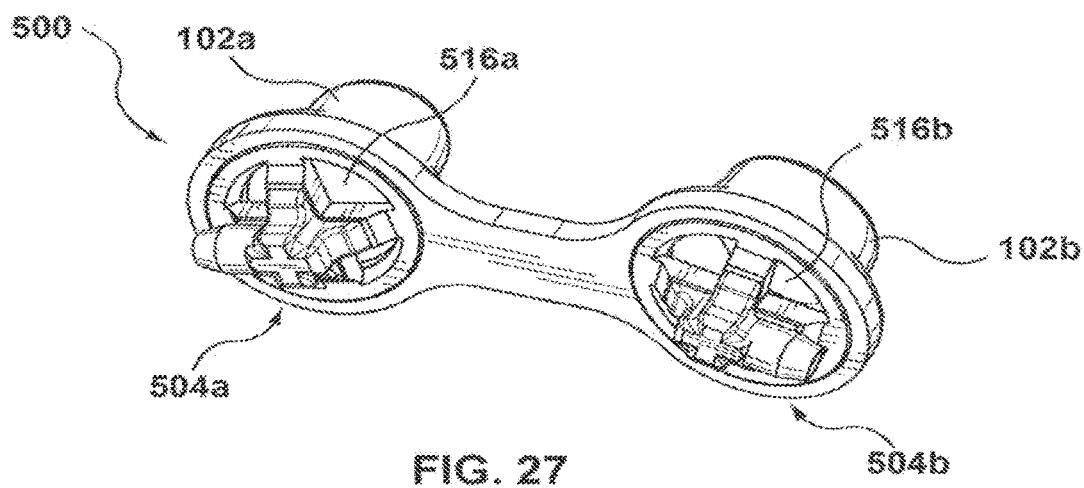
FIG. 27 is a perspective bottom view of the nasal interface device of FIGS. 24 and 25.

FIGS. 24 and 25 are exploded perspective views of a nasal interface device 500 in accordance with another embodiment hereof showing various subcomponents thereof, with FIG. 26 depicting a top view of nasal interface device 500 and FIG. 27 depicting a perspective bottom view of nasal interface device 500. The embodiment of FIGS. 24-27 may be used or adapted for use with all features described with reference to other embodiments hereof and only features and functions that differ from those already described will be detailed herein. Nasal interface 500 includes nasal pillow component 102 and a pair of hub components 504a, 504b. Each hub component 504a, 504b includes a distal support structure 508a, 508b, an X- or cross-shaped central hub 510a, 510b with a plurality of delivery openings 512a, 512b, X- or cross-shaped outlet discs 522a, 522b having a plurality of outlets 519a, 519b, X- or cross-shaped seals 524a, 524b and X- or cross-shaped proximal plenum structures 514a, 514b.

Respective annular rims 509a, 509b of hub components 504a, 504b, as described above, are attached to nasal pillow component 502 by gluing, welding or the like, and in another embodiment may include a series of post-forming apertures for receiving a material of nasal pillow component 102 there through in an over-molding process. A series of ambient air apertures 516a, 516b are formed between respective annular rims 509a, 509b, and X- or cross-shaped central hubs 510a, 510b.

Central hubs 510a, 510b of hub components 504a, 504b are positioned to longitudinally align with respective distal ports 101a, 101b of nasal pillows 102a, 102b such that the plurality of disc outlets 519a, 519b and delivery openings 512a, 512b of each hub are positioned to deliver a respiratory gas within its respective nasal pillow. Proximal plenum structures 514a, 514b of hub components 504a, 504b define an inlet 515a, 515b for receiving a respiratory gas from the respiratory assist device (not shown) and a plenum or chamber 517a, 517b for distributing the respiratory gas to the plurality of disc outlets 519a, 519b and delivery openings 512a, 512b of respective central hubs 510a, 510b. More particularly, a respective plenum 517a, 517b is formed when a proximal plenum structure 514a, 514b is secured or otherwise attached to a corresponding central hub 510a, 510b to be defined by proximal recesses 520a, 520b therebetween. Proximal plenum structures 514a, 514b are shaped and sized to snap or fit within corresponding proximal recesses 520a, 520b within central hubs 510a, 510b, to be secured therein by ultrasonic welding, gluing or the like.

The plurality of delivery openings 512a, 512b of each hub component 504a, 504b are periodically spaced along X- or cross-shaped distal face 521a, 521b of respective central hub 510a, 510b and are sized to be large enough to not impede on the flow exiting from a corresponding disc outlet 519a, 519b, as best shown in FIG. 26. Thus in the embodiment of FIGS. 24-27, the plurality of outlets 519a, 519b of outlet discs 522a, 522b directly correspond in number and arrangement to the plurality of delivery openings 512a, 512b of respective central hubs 510a, 510b. Outlet discs 522a, 522b and seals 524a, 524b are disposed within proximal recesses 520a, 520b of central hubs 510a, 510b such that the disc outlets 519a, 519b substantially align with corresponding central hub delivery openings 512a, 512b. In order to assure alignment of disc outlets 519a, 519b and delivery openings 512a, 512b, outlet discs 522a, 522b are held or pressed against respective proximal faces (not shown) of central hubs 510a, 510b by proximal plenum structures 514a, 514b being received within proximal recesses 520a, 520b to press seals 224a, 224b against an edge or perimeter of respective outlet discs 522a, 522b.

Figure 28:
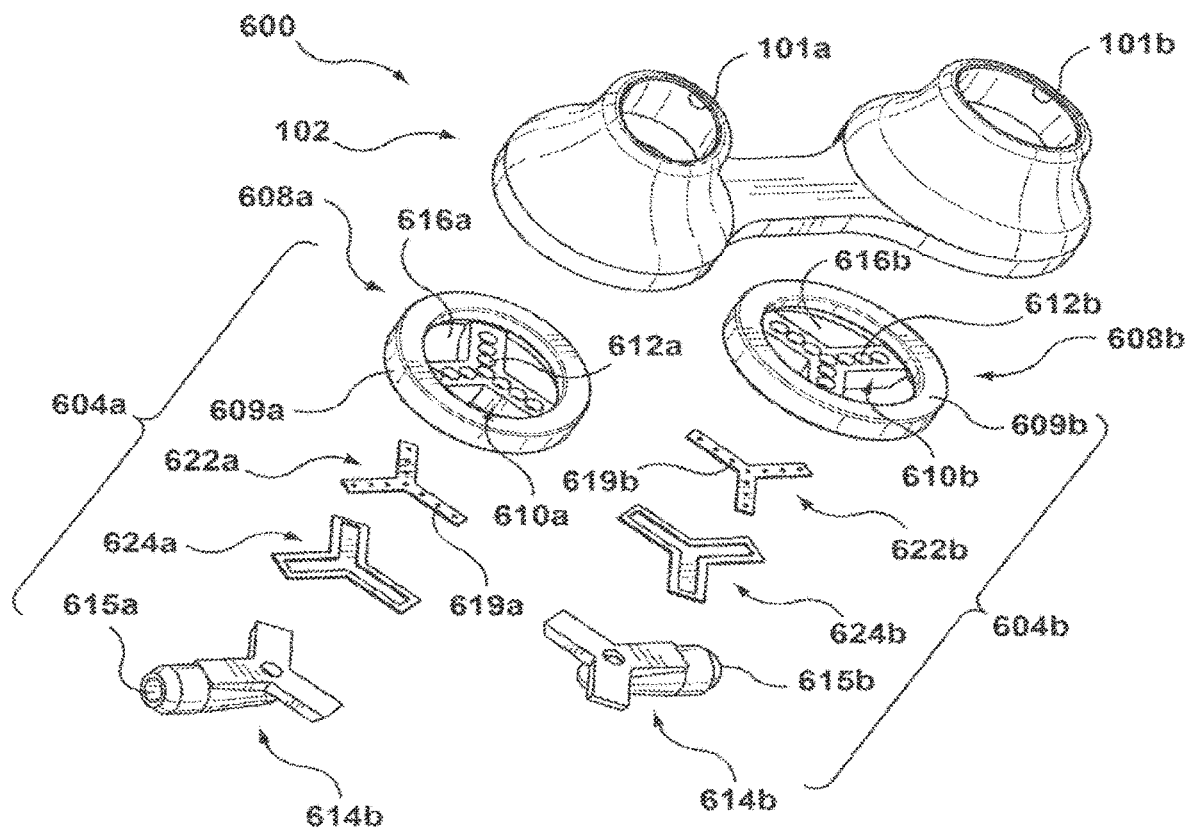
FIGS. 28 and 29 are exploded perspective views of a nasal interface device in accordance with another embodiment hereof showing various subcomponents thereof.
Figure 30:
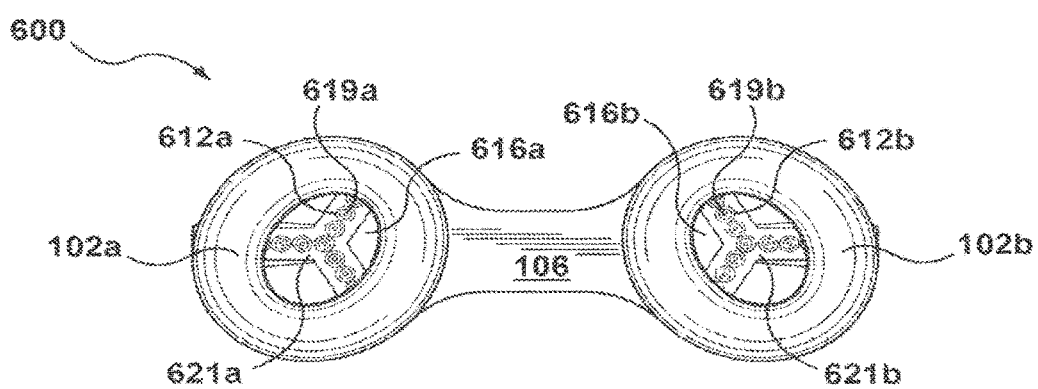
FIG. 30 is a top view of the nasal interface device of FIGS. 28 and 29.
Figure 29:
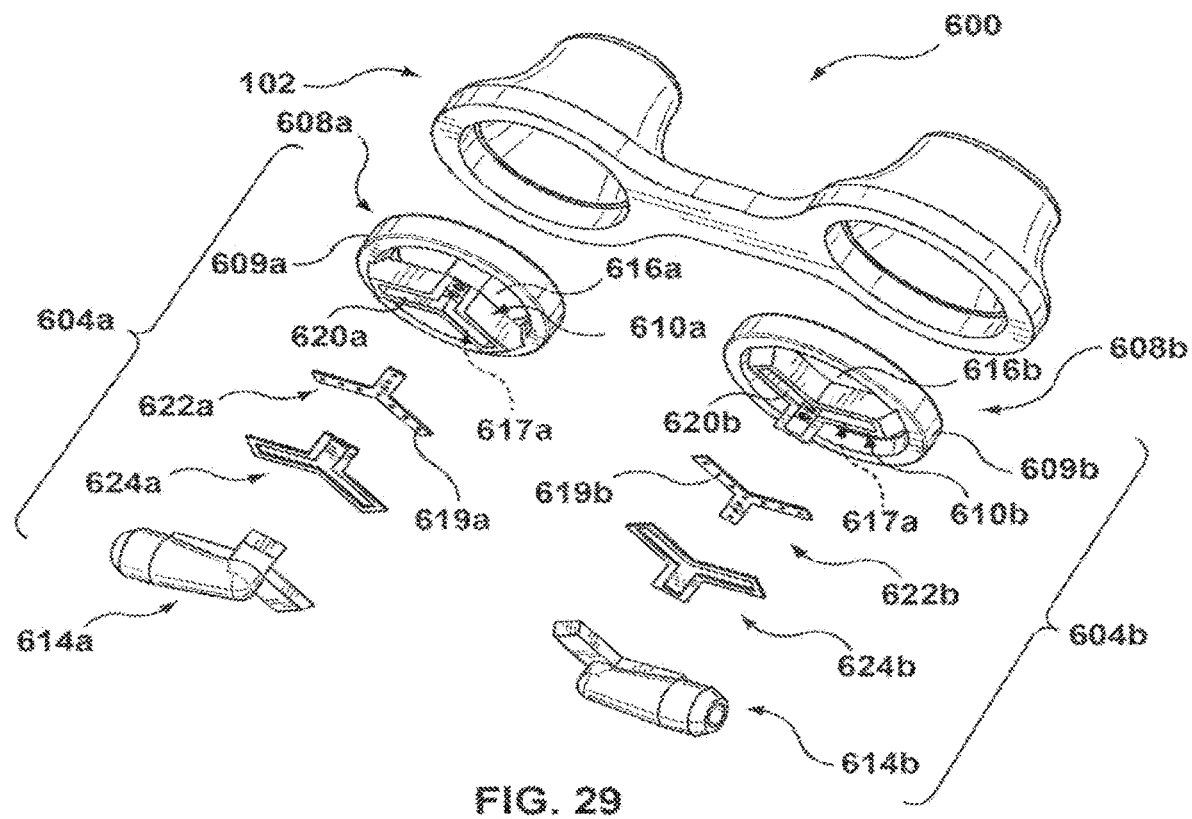
Figure 31:
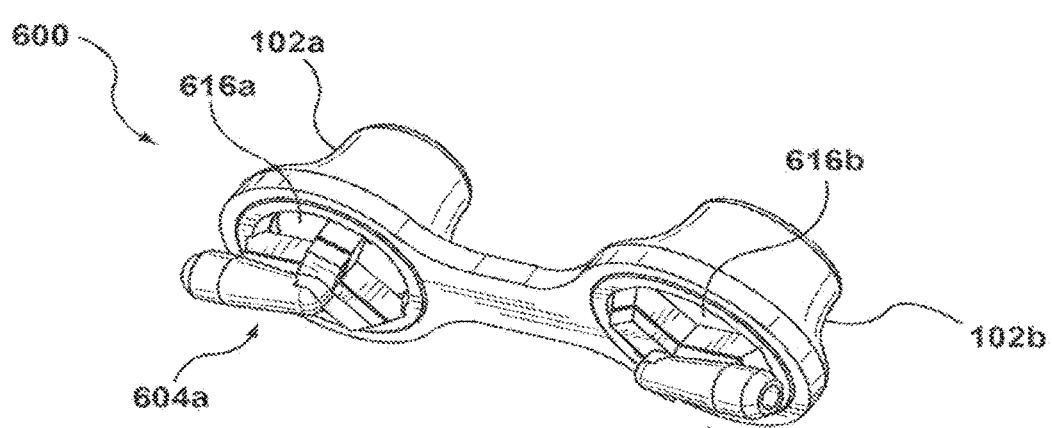
FIG. 31 is a perspective bottom view of the nasal interface device of FIGS. 28 and 29.

FIGS. 28 and 29 are exploded perspective views of a nasal interface device 600 in accordance with another embodiment hereof showing various subcomponents thereof, with FIG. 30 depicting a top view of nasal interface device 600 and FIG. 31 depicting a perspective bottom view of nasal interface device 600. The embodiment of FIGS. 28-31 may be used or adapted for use with all features described with reference to other embodiments hereof and only features and functions that differ from those already described will be detailed herein. Nasal interface 600 includes nasal pillow component 102 and a pair of hub components 604a, 604b. Each hub component 604a, 604b includes a distal support structure 608a, 608b, an Y-shaped central hub 610a, 610b with a plurality of delivery openings 612a, 612b, Y-shaped outlet discs 622a, 622b having a plurality of outlets 619a, 619b, Y-shaped seals 624a, 624b and Y-shaped proximal plenum structures 614a, 614b.

Respective annular rims 609a, 609b of hub components 604a, 604b, as described above, are attached to nasal pillow component 602 by gluing, welding or the like, and in another embodiment may include a series of post-forming apertures for receiving a material of nasal pillow component 102 there through in an over-molding process. A series of ambient air apertures 616a, 616b are formed between respective annular rims 609a, 609b, and Y-shaped central hubs 610a, 610b.

Central hubs 610a, 610b of hub components 604a, 604b are positioned to longitudinally align with respective distal ports 101a, 101b of nasal pillows 102a, 102b such that the plurality of disc outlets 619a, 619b and delivery openings 612a, 612b of each hub are positioned to deliver a respiratory gas within its respective nasal pillow. Proximal plenum structures 614a, 614b of hub components 604a, 604b define an inlet 615a, 615b for receiving a respiratory gas from the respiratory assist device (not shown) and a plenum or chamber 617a, 617b for distributing the respiratory gas to the plurality of disc outlets 619a, 619b and delivery openings 612a, 612b of respective central hubs 610a, 610b. More particularly, a respective plenum 617a, 617b is formed when a proximal plenum structure 614a, 614b is secured or otherwise attached to a corresponding central hub 610a, 610b to be defined by proximal recesses 620a, 620b therebetween. Proximal plenum structures 614a, 614b are shaped and sized to snap or fit within corresponding proximal recesses 620a, 620b within central hubs 610a, 610b, to be secured therein by ultrasonic welding, gluing or the like.

The plurality of delivery openings 612a, 612b of each hub component 604a, 604b are periodically spaced along Y-shaped distal face 621a, 621b of respective central hub 610a, 610b and are sized to be large enough to not impede on the flow exiting from a corresponding disc outlet 619a, 619b, as best shown in FIG. 30. Thus in the embodiment of FIGS. 28-31, the plurality of outlets 619a, 619b of outlet discs 622a, 622b directly correspond in number and arrangement to the plurality of delivery openings 612a, 612b of respective central hubs 610a, 610b. Outlet discs 622a, 622b and seals 624a, 624b are disposed within proximal recesses 620a, 620b of central hubs 610a, 610b such that the disc outlets 619a, 619b substantially align with corresponding central hub delivery openings 612a, 612b. In order to assure alignment of disc outlets 619a, 619b and delivery openings 612a, 612b, outlet discs 622a, 622b are held or pressed against respective proximal faces (not shown) of central hubs 610a, 610b by proximal plenum structures 614a, 614b being received within proximal recesses 620a, 620b to press seals 624a, 624b against an edge or perimeter of respective outlet discs 622a, 622b.

The nasal interface as described above may enable new therapeutic possibilities for ambulatory patient scenarios. In particular, it may be possible to achieve ambulatory dual therapy operation where both oxygen and ventilation therapy may be provided simultaneously.

In other embodiments, the nasal interface device may be used in combination with other gas sources, such as oxygen concentrators to provide dual therapy capability suitable for some applications. In some implementations, the higher efficiency entrainment and short delivery distance (low dead volumes) provided by the nasal interface devices disclosed herein allow lower operating pressures and the development of ventilation therapy airway pressures from lower overall source gas flow rates which are typical in oxygen gas sources.

Mechanical ventilation is typically prescribed to or needed by patients with late stage lung diseases or those with muscular diseases that affect the normal function of the diaphragm (Amyotrophic Lateral Sclerosis (ALS), muscular dystrophy and/or conditions from genetic abnormalities).

Mechanical ventilation provides a mechanical means to assist or control breathing as gas is moved in and out of the lungs through a mechanical ventilator connected directly to the patient. The patient is directly connected to the ventilator with a breathing circuit in which all of the inspiratory gas delivered to the patient is provided by the ventilator through the inspiratory limb and the patient's expiratory gas is controlled by the ventilator and exits through the expiratory limb of the breathing circuit.

Figure 32:
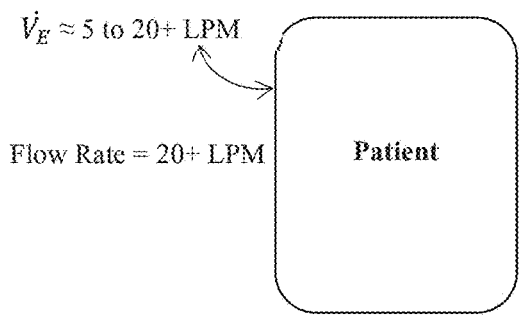
FIGS. 32-39 illustrate various aspects of ventilation and oxygen therapy scenarios.

A common measure for the ventilation rate of a patient is minute volume. Minute volume is a product of the average volume of the patient's breath (tidal volume) and breath rate (breaths/minute). Minute volume can be measured in terms of either inspired minute volume ($\dot{V}_i$) or expired minute volume ($\dot{V}_E$). Expiratory volume is generally an easier measurement for a clinician to capture so the common measurement for tidal volume is expiratory tidal volume ($V_{te}$) and expired minute volume ($\dot{V}_E$). The nominal range of expired minute volumes ($\dot{V}_E$) for a healthy patient are ~5 to 8 LPM while resting, up to 12 LPM during light activity, and ~20 to 60 LPM during moderate exercise. Patients with chronic pulmonary diseases such as COPD commonly have twice the resting minute volume of a healthy person, $\dot{V}_E \approx 8$ to 16 LPM. FIG. 32 schematically illustrates spontaneous breathing for an adult patient with no therapy.

There have been several techniques derived to ventilate a lung (for example, utilization of an iron lung, negative pressure, positive pressure, high frequency, etc.), however the prevailing approach has been the delivery of positive pressure ventilation which can be in the form of continuous positive airway pressure (CPAP), bi-level (Bi PAP), volume/pressure assist, volume/pressure control, assist/control, spontaneous intermittent mandatory ventilation (SIMV), etc. Positive pressure mechanical ventilation has evolved over the decades with sophisticated devices, delivery modes and algorithms, however all examples do one basic thing, ventilate a patient's lungs.

Figure 33:
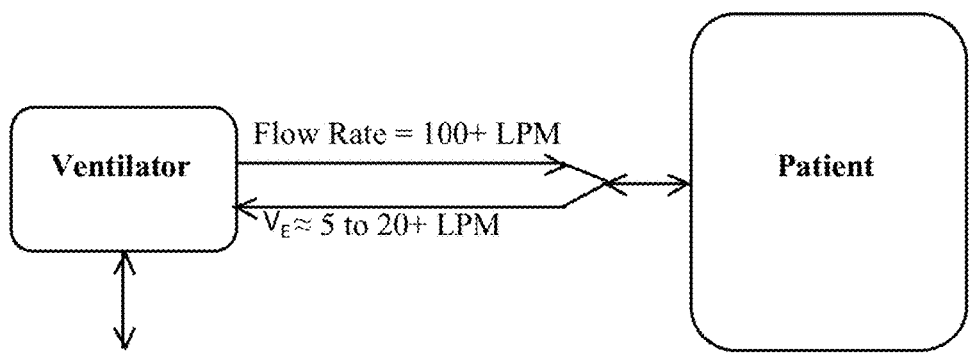

Positive pressure ventilators generate flows in the range of ~20 to 100+ LPM in order to ensure that the patient's inspiratory needs are met. FIG. 33 illustrates exemplary parameters for a patient on support or control mechanical ventilation. Some examples of portable positive pressure ventilators on the market today are the Vyaire™ LTV™ series ventilators (14 lbs, 10"×12"×3"), the ReVel® ventilator (9.5 lbs, 11.3"×7.1"×3.3").

Oxygen therapy is typically prescribed to patients that have lung conditions that prevent the lungs from adequately absorbing oxygen, including chronic obstructive pulmonary disease (COPD), interstitial lung disease (ILD), pneumonia, asthma, etc. Oxygen therapy is usually prescribed if a patient's blood oxygen level is less than or equal to 55 mg Hg or their oxygen saturation level is 88% or lower. Oxygen therapy is typically administered through a two-pronged nasal cannula or a face mask. Oxygen sources primarily include hospital/facility walls, liquid oxygen dewars, compressed oxygen cylinders and oxygen concentrators. Liquid oxygen dewars, compressed oxygen cylinders and oxygen concentrators are the only options that provide some level of portability for an ambulating patient. Liquid oxygen dewar options are still present in the United States, however they are slowly being phased out due to high costs associated with manufacturing, distribution and storage. Compressed oxygen continues to be readily available in the United States although its cost of distribution (frequent deliveries) is placing more emphasis on providing patients with an oxygen concentrator that can remain in the home for several years with infrequent servicing and delivery requirements. Oxygen concentrators utilize a process called pressure swing adsorption, PSA or vacuum pressure swing adsorption VPSA to separate the nitrogen from the ambient air and deliver the oxygen to the patient. The operating principles of these processes are not discussed herein.

Best practices in oxygen therapy require oxygen concentrators output nominally 90% oxygen concentration. In addition, FDA and ISO regulatory guidance standards also require that the concentration output of concentrators to be above a certain limit, typically >85%, in order to meet the needs of an oxygen prescription from a physician. As such, oxygen concentrators are intentionally designed to output nominally 90% of oxygen concentration under all settings, in order to meet regulatory clearance and government reimbursement requirements.

There are three classes of oxygen concentrators: stationary, transportable and portable. The output flow rate of each class of concentrator varies significantly and correspondingly, so does their respective size and weight.

Figure 34:
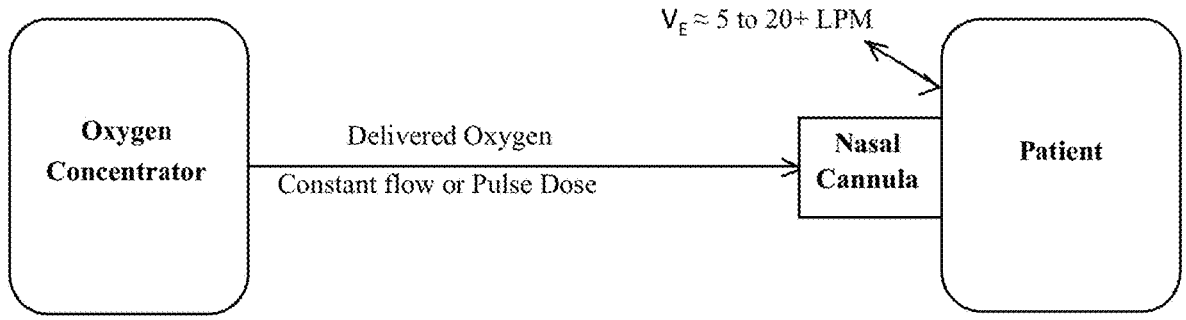

A typical configuration of an oxygen concentrator and patient using a nasal cannula is schematically shown in FIG. 34. The oxygen concentrator is connected to a two-pronged nasal cannula or facemask that is worn by the user. The concentrated oxygen is conveyed through oxygen tubing and delivered to the patient in either constant flow or pulse dose manner. The patient exhales through a secondary path, either out of their mouth or around the nasal prongs if exhaling through the nose. Either constant flow oxygen or an inspiratory triggered, timed pulse dose of oxygen, commonly known as pulse dose, is supplied to the patient via a nasal cannula or facemask.

Constant flow and pulse dose therapies only provide elevated oxygen concentrations to the patient and do not provide either positive or negative pressure ventilation to the patient.

Stationary concentrators are heavy and bulky (typically ~40 lbs) and are designed to reside in a central location on the floor in a patient's home. Ambulation when using a stationary concentrator is possible within the home with the use of a ~50 ft oxygen tube. Stationary devices are typically designed to deliver an adjustable constant flow rate of up to 5 LPM to 15 LPM.

Transportable concentrators are smaller than their stationary counterparts however, they are still too big to carry when ambulating. Transportable concentrators are typically integrated into a rolling cart design so that the user can pull the device along with them as they ambulate. Transportable devices are typically designed to deliver an adjustable constant flow rate of up to 2 LPM to 3 LPM, with 3 LPM being more of the standard. Transportable devices also provide pulse dose therapy. The bolus sizes are scaled within a range such that the product of the bolus size and breath rate do not exceed the oxygen generation rate of the device.

Portable devices are smaller and lighter weight than stationary or transportable devices and thus are typically worn by the user via a shoulder strap or backpack. Portable devices weigh approximately 5 to 7 lbs (see Table 1 below). However, as the size and weight of portable oxygen concentrators are reduced, the oxygen generating capabilities are also reduced. Portable concentrators typically only output 0.5 to 1.25 LPM of oxygen in continuous flow. However their spontaneous flow rates, which are a fraction of the breath cycle may be much higher depending on how the flow is managed. The pulse dose bolus' are inspiratory triggered, time controlled and the volume of delivered oxygen is usually in the range of 10 to 50 mL depending on the setting. The delivered flow rate during the bolus is usually 10 LPM.

TABLE 1

| | Respironics SimplyGo Mini | Inogen One G3 | Caire FreeStyle Comfort | GCE Zen-O Lite | Invacare Platinum Mobile | Inogen One G2 |
|---|---|---|---|---|---|---|
| Output (LPM) | 1.00 | 1.05 | 1.05 | 1.05 | 0.88 | 1.26 |
| Weight (lb) | 5 lb | 4.8 lb | 5 lb | 5.5 lb | 4.9 lb | 7 lb |
| lb/LPM | 5.0 | 4.6 | 4.8 | 5.2 | 5.6 | 7.0 |
| Average lb/LPM | | | 5.4 | | | |

Given the industry has standardized on the nominal 90% oxygen concentration delivered to the patient, portable oxygen concentrators will limit the net delivery output to the patient based on their oxygen production capacity. Methods employed to limit the oxygen delivery output are to limit the maximum breath rate for a given bolus size and/or to reduce the bolus size in proportion to the breath rate. For example, a 1 LPM portable oxygen concentrator would only be able to deliver 20 breaths per minute (BPM) at a bolus size of 50 ml (20 BPM*0.05 L=1 LPM). The product of the bolus volume and the breath rate is defined as delivered oxygen minute volume.

Most adults have inspiratory tidal volumes in the range of 300 to 1,000 mL+ with flow rates of 20 to 100+ LPM. Since patients require significantly more flow and volume than what the concentrator delivers, the balance of volume is ambient air that is inspired by the patient into the nares around the nasal cannula or through the patient's mouth. The bolus from the concentrator elevates the fractional inspired oxygen ($FIO_2$) level that is delivered to the patient, which is intended to elevate their blood oxygen saturation, however it does not elevate the pressure in the nares. Without pressure generation, mechanical ventilation cannot occur.

Aside from delivering just concentrated oxygen or mechanical ventilation directly to a patient as discussed above, some patients may benefit from a combination of elevated $FIO_2$ and ventilation, and this may be of particular importance to support ambulatory patients, or to increase the therapeutic effectivity to help patients maintain or achieve ambulatory lifestyles which would otherwise be unavailable.

Figure 35:
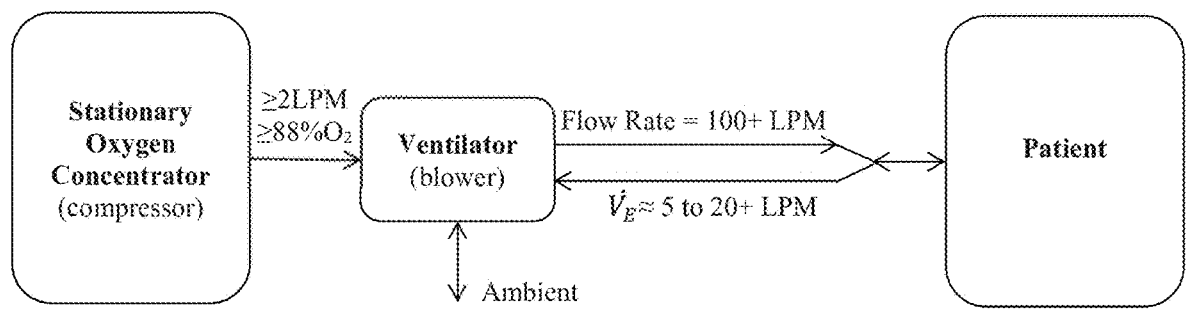

In order to provide this therapy, i the output of a constant flow stationary oxygen concentrator (2 LPM) can be connected to a system that is providing positive pressure ventilation to a patient (see FIG. 35). This can be done by connecting the output of the oxygen concentrator to a patient breathing circuit and 'bleed-in' a prescribed amount of concentrated oxygen minute volume into the breathing circuit in effort to increase the $FIO_2$ to the patient. Some ventilators are equipped with low pressure oxygen inlet ports for connection to an oxygen concentrator, in which case the ventilator mixes the inlet air with the oxygen and deliver the mixture to the patient through the breathing circuit. FIG. 35 shows a configuration where the output of the oxygen concentrator is connected a positive pressure ventilator.

The combination of ventilation and elevated delivered oxygen therapies provide physicians with additional treatment options for their patients that have various lung diseases. However, the oxygen flow rate required to get sufficient $FIO_2$ delivered to the patient is typically greater than 2 LPM constant flow. Given the state-of-the-art, only transportable and stationary concentrators provide this type and level of oxygen output. Portable oxygen concentrators only provide pulse dose oxygen therapy upon detection of a patient inspiratory effort and may not synchronize properly when attached to a traditional mechanical ventilator breathing circuit as schematically illustrated in FIG. 35. As a result, the most portable configuration option would be a transportable oxygen concentrator coupled with a portable mechanical ventilator which would be cumbersome to manage in a portable setting and would most likely end up in a stationary configuration. This would prohibit the patient from effectively ambulating, participating in pulmonary rehabilitation and performing daily acts of living.

Figure 36:
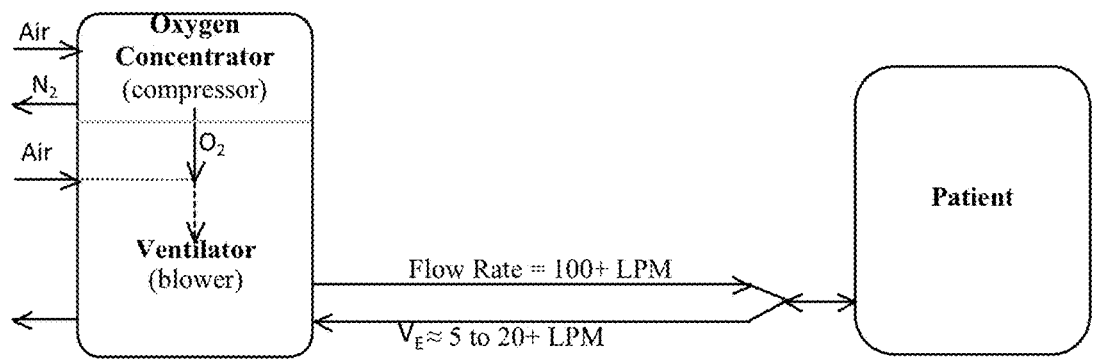

Some efforts have been made to incorporate an oxygen concentrator into a mechanical ventilator as disclosed in U.S. Patent Pub. No. 2016/0279362 to DeVries et al. The device that is disclosed in Devries is a concentrator and a mechanical ventilator contained within the same enclosure and weighs over 18 lbs. An arrangement as disclosed in DeVries is schematically shown in FIG. 36.

Although both a concentrator and a ventilator are contained in the same enclosure, the concentrator operates relatively independent of the mechanical ventilator portion of the device and with limited sharing and/or integration of hardware, which results in an expensive and complex device. This is due in part of the fact that oxygen concentrators require significantly higher operating pressures than mechanical ventilators to operate the PSA process and that mechanical ventilators require much higher flow rates to ventilate a patient than the compressors for oxygen concentrators can output. Oxygen concentrators operate at pressures in the 20 PSIG range, whereas typical mechanical ventilators only need to deliver pressures much less than 2 PSIG. In addition, the compressors for oxygen concentrators produce roughly ~16 LPM of air for every 1 LPM of oxygen produced (1 LPM $O_2$/21% $O_2$ in air/30% recovery), whereas mechanical ventilators require up to 100 to 300 LPM of flow depending on the types of ventilation modes they provide. The device disclosed in DeVries produces only 1 to 1.5 LPM of oxygen (nominally 1.25 LPM) requiring a compressor flow rate of ~20 LPM (16 LPM/LPM $O_2$*1.25 LPM $O_2$), roughly an order of magnitude below the required flow rates for mechanical ventilation. As such, this device requires a compressor for the concentrator and a centrifugal blower for the ventilator portion.

The vast difference in flow and pressure requirements of an oxygen concentrator and mechanical ventilator make it difficult to select a single portable air source to supply both systems. Portable mechanical ventilators typically utilize a centrifugal fan which provide the required high flows but only provide limit pressures (<2 PSIG) and are not sufficient enough to support the PSA adsorption process (~20 PSIG). Conversely, oxygen concentrators typically utilize a reciprocating wobble piston compressor which provides compressed air in a cost effective and efficient manner at the pressure levels required to support the PSA adsorption process. Although piston compressor technology can be scaled to deliver up to 300 LPM, the size, weight and power requirements for a compressor this size are not conducive to a portable device (>>10 lbs).

The device disclosed in DeVries weighs over 18 lbs, which although portable, cannot be carried for long periods of time by the user for ambulation. Typical portable, user-carried devices weigh less than 9 lbs. Moreover, state-of-the-art portable oxygen concentrators that deliver 1 LPM of oxygen weigh 6 lbs. This example shows that the state-of-the-art designs of systems that incorporate oxygen generation and mechanical ventilation are far from being portable for a user to carry and ambulation on their own.

Lightweight, portable oxygen concentrators for ambulatory patients are traditionally not used as a gas source for mechanical ventilators because they typically are not capable of providing the flow and pressure requirements of a mechanical ventilator. As such, most portable oxygen concentrator patients do not have a way to augment the tidal volume and must rely solely on the increased $FiO_2$ provided by the oxygen concentrator. The oxygen gas flow without any significant pressure assistance from portable oxygen concentrators may not be sufficient for some patients with respiratory deficiencies.

Certain embodiments disclosed herein provide a non-invasive air entrainment and portable oxygen concentrator system that can be used to entrain ambient air in oxygen enriched gas from the oxygen concentrator during a patient's spontaneous breathing so as to augment the inspiratory tidal volume of the patient. In one embodiment, the non-invasive air entrainment and portable oxygen concentrator system utilizes a small lightweight nasal pillow interface, embodiments of which are described herein, and a lightweight oxygen concentrator weighing less than 9 lbs. The oxygen concentrator is tuned to provide sufficient flow rate to the nasal pillow interface to meet the inspiratory flow rate required for the patient. In some implementations, the output flow rate of the portable oxygen concentrator compressor is tuned to be at least 20 LPM and the non-invasive air entrainment device entrains ambient air to augment the flow rate of the inspiratory gas to at least 100 LPM. In some implementations, the output flow rate of the portable oxygen concentrator compressor is adjustable in accordance with the inspiratory flow rate requirement for the patient. For example, the inspiratory flow rate requirement for an ambulatory patient in an early stage of respiratory disease may be lower than 100 LPM. In some implementations, the nasal pillow interface can be directly connected to the nasal cannula tubing port on the oxygen concentrator. In some implementations, the low profile nasal interfaces disclosed herein can enable single lumen sensing and delivery capabilities utilized in current portable oxygen concentrators, in contrast to NIOV systems.

Advantageously, the lightweight non-invasive air entrainment and portable oxygen concentrator system utilizes a singular compressed air generating source that can provide both mechanical ventilation and elevated levels of oxygen concentration to a patient without requiring any invasive mechanical devices, face masks, nasal masks or the like. The small, lightweight nasal pillow interface works with the oxygen concentrator to increase the tidal volume of the oxygen enriched gas by entraining ambient air to provide a boost to the patient. In some implementations, the system is adaptive in that the tidal volume can be adjusted by tuning the flow rate of the oxygen concentrator.

In another embodiment, a small lightweight nasal pillow interface apparatus and system used for delivering respiratory gas to a patient through a portable oxygen concentrator is provided. The interface increases the velocity of the delivered respiratory gas within the assembly. The configuration and placement of the high velocity respiratory gas relative to ambient air ports facilitates entrainment of ambient air proximal to the inlet of the nasal interface utilizing the venturi principle. The interface can generate up to 300 to 400% of ambient air entrainment. The interface apparatus converts a relatively low respiratory gas flow rate, <30 LPM, into a high delivered flow of 100+ LPM to the patient. In addition, certain embodiments of the interface described herein can generate a positive pressure of up to $18 cmH_2O$, however it can be scaled to deliver more or less positive pressure.

Figure 37:
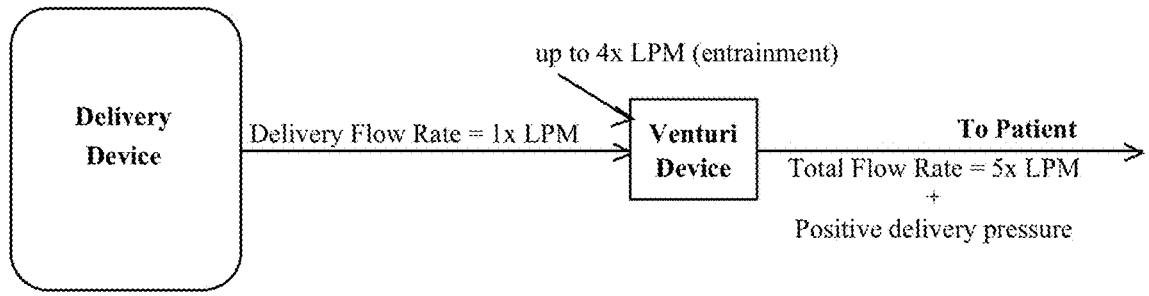

FIG. 37 shows the net effect of the flow amplification due to entrainment using an exemplary amplification factor of 5×.

The entrained ambient air amplifies the flow delivered in addition to providing positive pressure to the patient. The nasal interface can be coupled to an inspiratory triggered, time cycled delivery device that, in combination, can provide positive pressure ventilation. Such a triggered device may take the form of a portable oxygen concentrator with conserver functionality.

The portable oxygen concentrator's ventilation capabilities may be governed by the peak flow rate of oxygen gas delivered by the conserver during the onset of inhalation. This peak flow rate occurs for a brief period of less than 1 second and may be nominally between 10 LPM and 20 LPM. The venturi device would then amplify this peak flow rate to generate ventilation therapy via elevated airway pressure and flow above that derived from the oxygen bolus itself. Additionally, the portable oxygen concentrator may be further tuned to provide expanded ventilation therapy by passing more air from the compressor through the system to increase the peak flow rate and associated entrainment system by altering the compressor sizing or speed control. In this embodiment, the oxygen may be diluted by the supplemental air flow, but the greater ventilation therapy may still result in improved overall therapy to the patient. In this scenario the same portable oxygen concentrator would be capable of operating in multiple ventilation modes to provide varying levels of ventilation support from the same oxygen production capacity.

If the peak flow rate of the delivered oxygen bolus is in the range of 10 LPM to 20 LPM, the resulting 5× amplification of the delivery device can reach peak flow rates of 50 LPM to 100 LPM.

Figure 38:
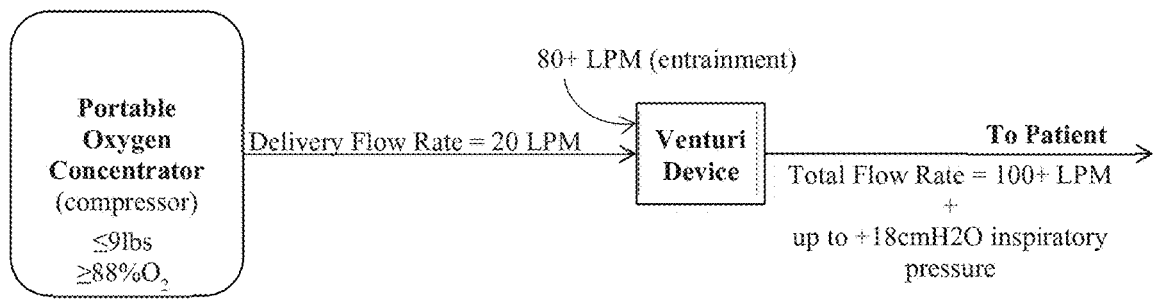

As mentioned above, general compressor requirements for a portable oxygen concentrator are roughly 16 LPM of air for every 1 LPM of oxygen production. If a venturi device is connected to an 1 LPM portable oxygen concentrator with a compressor capable of delivering 16 LPM and additional compressed gas from the compressor is supplied to the device output, then the total flow rate delivered to a patient could exceed the 50-100+ LPM with consideration of the amplification factor due to entrainment as discussed above as an alternate operating mode for a portable oxygen concentrator. As discussed herein, most adults have inspiratory flow rates of up to 100 LPM. In order for a venturi nasal interface sized that is as described herein (5× total flow rate) to supply the required flow rate to a patient, the flow rate from the delivery device would be around 20 LPM (100 LPM/5). FIG. 38 schematically illustrates a venturi device (preferably the disclosed noninvasive nasal interface device described herein, but alternatively, more traditional ventilation interfaces such as non-invasive masks or invasive tracheal tubes) connected to a portable oxygen concentrator.

Figure 39:
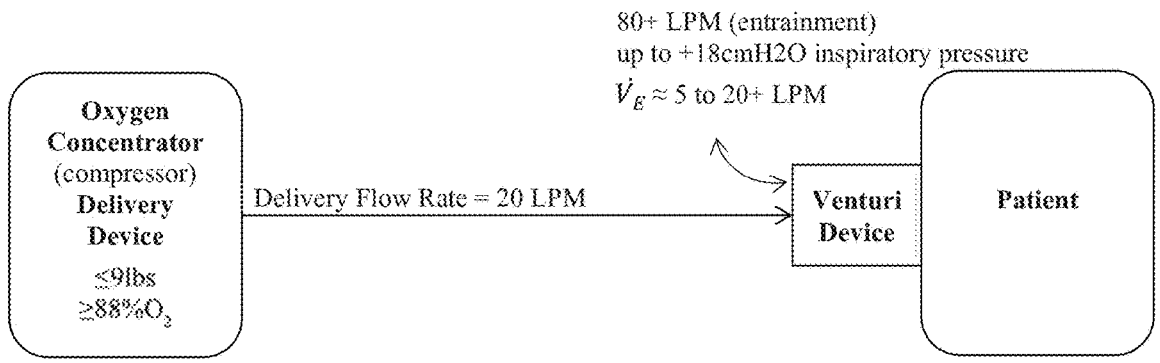

In order to reach 20 LPM of delivered flow, the compressor can be oversized or run at a higher RPM relative to the desired oxygen output, for example, a 1 LPM concentrator which would otherwise only need 16 LPM. In a second configuration, an oxygen concentrator can be sized to output 1.25 LPM $O_2$ which would require a compressor flow rate of 20 LPM (20 LPM/16 LPM/LPM $O_2$). The additional flow-rate available from an overproducing compressor can be directed to increase the peak gas flow rate delivered by the portable concentrator to increase the ventilation therapy capability. A third option could be the addition of a volume accumulator at the outlet of the concentrator that would store pressurized gas during the exhalation periods of the breath cycle and be used to supplement the flow from the compressor during the delivery period (the inspiratory phase). Assuming the current state-of-the-art oxygen output weight densities (5.4 lb/LPM), the 1 LPM oxygen output concentrator that would provide mechanical ventilation when coupled to a venturi based ventilation interface, would weigh only 5.4 lbs, and the 1.25 LPM example would weigh only 6.75 lbs, making both options wearable (<9 lbs for a wearable device). Such an arrangement is schematically shown in FIG. 39.

These examples demonstrate that the nominal output of a compressor in a portable and wearable oxygen concentrator can empower a venturi device to provide ample levels of mechanical ventilation to a patient and elevated levels of oxygen concentration. While the current state of the art requires either coupling an oxygen concentrator to a ventilator either externally, or within the same enclosure as described in DeVries, both of these options do not result in a portable and wearable solution (for example, because the device weighs over 18 lbs). Thus, advantageously, utilization of an entrainment device (such as that described herein) alongside a portable oxygen concentrator can provide sufficient amounts of mechanical ventilation to a patient and oxygen to a patient without the need for a ventilator device.

As shown, compressors are readily available in a weight/size form can provide ample pressure and flow to power a portable and wearable oxygen concentrator. Ample flow (up to 100 LPM) can be achieved if it is desired to ventilate a patient with a portable oxygen concentrator if mated with a suitable entrainment device, such as that described herein. Sufficient flow rates (up to 100 LPM) needed to mechanically ventilate a patient can be provided by connecting a small lightweight nasal pillows interface venturi apparatus to a portable and wearable oxygen concentrator.

It should be noted that beneficial flow can be achieved by interfacing an entrainment device such as the herein described nasal pillow device to existing ultra-low weight portable concentrators. As noted above, currently available peak flow rates of 10-20 LPM of oxygen delivery pulses which would be amplified to 50-100 LPM with the nasal pillow entrainment interface, is achievable from an ultra-low weight concentrator. Even small design tweaks and tuning could increase this flow rate. So for ambulatory patients, who may be on the low end of ventilation requirements, such an approach can yield immediate and highly beneficial dual therapy conditions. Additionally, patients who require more traditional ventilation interfaces such as masks or tracheal tube interfaces may still benefit from the increased ambulation provided by the portable oxygen concentrator combined with small tubing size and highly efficient venturi system of the invention.

While various embodiments have been described above, it should be understood that they have been presented only as illustrations and examples of the present invention, and not by way of limitation. It will be apparent to persons skilled in the relevant art that various changes in form, shape, arrangement and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system for providing oxygen and mechanical ventilation therapy to an ambulatory patient, the system comprising:
   a nasal interface apparatus comprising:
      a pair of nasal pillows, each of the pair of nasal pillows configured to be secured at least partially within a nostril of the patient and having a first end and a second end opposite the first end, the second end configured to be positioned farther inside the nostril when the nasal interface apparatus is in use; and
      a pair of hub components, each of the pair of hub components arranged at the first end of one of the pair of nasal pillows and configured to receive oxygen-enriched gas from one of a pair of tubes of the system, each of the pair of hub components comprising one or more delivery openings configured to direct the oxygen-enriched gas toward the second end of the one of the pair of nasal pillows; and
   a portable oxygen concentrator (POC) comprising:
      a compressor configured to receive and compress ambient air, the compressor further configured to output the compressed ambient air;
      a gas separation member; and
      an outlet connected to said pair of tubes;
   wherein:
      the POC is configured to guide a first portion of the compressed ambient air to the gas separation member and guide a second portion of the compressed ambient air to bypass the gas separation member and flow to said outlet;
      the gas separation member produces an oxygen-enriched gas based on the first portion of the compressed ambient air;
      the outlet is configured to guide the oxygen-enriched gas and the second portion of the compressed ambient air to the pair of tubes, the pair of tubes configured to guide the oxygen-enriched gas and the second portion of the compressed ambient air directly to the pair of hub components of the nasal interface apparatus;
      the nasal interface apparatus is configured to entrain ambient air in conjunction with the oxygen-enriched gas received from the POC; and
      the POC is further configured to provide varying levels of ventilation support and oxygen enrichment to the patient when ambulating by varying an amount of the second portion of the compressed ambient air bypassing the gas separation member.

2. The system of claim 1 wherein the POC weighs at least one of less than 11 pounds or less than 9 lbs.

3. The system of claim 1 wherein a maximum compressor output flow rate is at least one of greater than 10 Liters Per Minute (LPM) or greater than 20 LPM, and wherein a maximum ventilation gas flow rate to the patient is at least one of greater than 30 LPM, greater than 60 LPM, or greater than 100 LPM.

4. The system of claim 1 wherein a total gas flow output of the POC is 20 Liters Per Minute (LPM) or less per liter of oxygen produced, and wherein the POC weighs 6.75 pounds or less.

5. The system of claim 1 wherein a flow amplification rate due to air entrained by the nasal interface apparatus is 5 times.

6. The system of claim 1 wherein the POC has a peak concentrated oxygen flowrate output of between 10 and 20 Liters Per Minute (LPM) when delivered synchronously with an onset of inspiration of the patient.

7. The system of claim 1 wherein the POC has a peak concentrated oxygen flowrate output of greater than 20 LPM when delivered synchronously with an onset of inspiration of the patient.

8. The system of claim 1 wherein a total gas flow output of the POC is 16 LPM or less per liter of oxygen produced, and wherein the POC weighs 5.4 pounds or less.

9. The system of claim 1 wherein the one or more delivery openings comprises a plurality of delivery openings.

10. The system of claim 1 wherein the POC weighs between 5 and 7 pounds.

\* \* \* \* \*